United States Patent
Qiu et al.

(10) Patent No.: US 12,178,063 B2
(45) Date of Patent: Dec. 24, 2024

(54) ORGANIC LIGHT EMITTING DEVICE AND DISPLAY APPARATUS

(71) Applicant: BOE Technology Group Co., Ltd., Beijing (CN)

(72) Inventors: Lixia Qiu, Beijing (CN); Lei Chen, Beijing (CN); Yang Liu, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 658 days.

(21) Appl. No.: 17/429,359

(22) PCT Filed: Dec. 24, 2020

(86) PCT No.: PCT/CN2020/138927
§ 371 (c)(1),
(2) Date: Aug. 9, 2021

(87) PCT Pub. No.: WO2022/082990
PCT Pub. Date: Apr. 28, 2022

(65) Prior Publication Data
US 2022/0320455 A1    Oct. 6, 2022

(51) Int. Cl.
*H10K 50/18* (2023.01)
*C07C 15/28* (2006.01)
(Continued)

(52) U.S. Cl.
CPC ............. *H10K 50/18* (2023.02); *C07C 15/28* (2013.01); *C07D 213/16* (2013.01);
(Continued)

(58) Field of Classification Search
CPC ........ H10K 2101/30; H10K 2101/40
See application file for complete search history.

(56) References Cited

U.S. PATENT DOCUMENTS

2017/0179396 A1  6/2017  Kim et al.
2017/0179397 A1  6/2017  Kim et al.
(Continued)

FOREIGN PATENT DOCUMENTS

CN    106981576 A    7/2017
CN    110028523 A    7/2019
(Continued)

OTHER PUBLICATIONS https://www.sciencedirect.com/topics/engineering/carrier-mobility (2018).*

*Primary Examiner* — Vu A Nguyen
(74) *Attorney, Agent, or Firm* — Ling Wu; Stephen Yang; Ling and Yang Intellectual Property

(57) ABSTRACT

Provided are an organic light emitting device and a display apparatus. The organic light emitting device includes an anode, a cathode, and an emitting layer disposed between the anode and the cathode, wherein the emitting layer includes a host material and a dopant material doped in the host material; the host material and the dopant material satisfy:

$$|HOMO_{Dopant}| < |HOMO_{Host}|,$$
$$|LUMO_{Dopant}| < |LUMO_{Host}|;$$

wherein, $HOMO_{Dopant}$ is a highest occupied molecular orbit (HOMO) energy level of the dopant material, $HOMO_{Host}$ is a HOMO energy level of the host material, $LUMO_{Dopant}$ is a lowest unoccupied molecular orbital (LUMO) energy level of the dopant material, and $LUMO_{Host}$ is a LUMO energy level of the host material.

16 Claims, 6 Drawing Sheets

(51) Int. Cl.

| | |
|---|---|
| *C07D 213/16* | (2006.01) |
| *C07D 239/26* | (2006.01) |
| *C07D 251/24* | (2006.01) |
| *C07D 307/91* | (2006.01) |
| *C07D 405/04* | (2006.01) |
| *C07D 405/12* | (2006.01) |
| *C07D 487/04* | (2006.01) |
| *C07F 5/02* | (2006.01) |
| *H10K 50/11* | (2023.01) |
| *H10K 50/12* | (2023.01) |
| *H10K 85/30* | (2023.01) |
| *H10K 85/60* | (2023.01) |
| *H10K 101/40* | (2023.01) |

(52) U.S. Cl.
CPC ......... *C07D 239/26* (2013.01); *C07D 251/24* (2013.01); *C07D 307/91* (2013.01); *C07D 405/04* (2013.01); *C07D 405/12* (2013.01); *C07D 487/04* (2013.01); *C07F 5/027* (2013.01); *H10K 85/322* (2023.02); *H10K 85/615* (2023.02); *H10K 85/631* (2023.02); *H10K 85/654* (2023.02); *H10K 85/6572* (2023.02); *H10K 85/6574* (2023.02); *H10K 85/6576* (2023.02); *C07B 2200/05* (2013.01); *H10K 50/11* (2023.02); *H10K 50/12* (2023.02); *H10K 2101/40* (2023.02)

(56) References Cited

U.S. PATENT DOCUMENTS

| | | |
|---|---|---|
| 2019/0181350 A1 | 6/2019 | Hatakeyama et al. |
| 2020/0127212 A1* | 4/2020 | Adamovich ........... C09K 11/06 |
| 2020/0172558 A1* | 6/2020 | Joo ..................... H10K 85/6572 |
| 2021/0028365 A1 | 1/2021 | Tasaki et al. |

FOREIGN PATENT DOCUMENTS

| | | | | |
|---|---|---|---|---|
| CN | 111253421 | A | 6/2020 | |
| KR | 2148296 | B1 * | 8/2020 | ............ C07F 5/027 |
| WO | 2019194298 | A1 | 10/2019 | |
| WO | 2020080416 | A1 | 4/2020 | |
| WO | 2020111830 | A1 | 6/2020 | |
| WO | 2020117026 | A1 | 6/2020 | |

* cited by examiner

ORGANIC LIGHT EMITTING DEVICE AND DISPLAY APPARATUS

CROSS-REFERENCE TO RELATED APPLICATIONS

The present application is a U.S. National Phase Entry of International Application No. PCT/CN2020/138927 having an international filing date of Dec. 24, 2020, which claims the priority to International Application No. PCT/CN2020/123375 filed with the CNIPA on Oct. 23, 2020 and entitled "Organic Light Emitting Device and Display Apparatus". The above-identified applications are incorporated herein by reference in their entirety.

TECHNICAL FIELD

The present disclosure relates to, but is not limited to, the field of display technologies, in particular to an organic light emitting device and a display apparatus.

BACKGROUND

An organic Light Emitting Device (OLED) is an active emitting device, which has advantages of high brightness, color saturation, ultra-thin, a wide viewing angle, low power consumption, extremely high response speed, flexibility, etc., and is widely applied in the field of panel displays.

An OLED includes an anode, a cathode, and an emitting layer disposed between the anode and the cathode. A light emitting principle of the OLED is that holes and electrons are injected into the emitting layer from the anode and the cathode respectively. When the electrons and holes meet in the emitting layer, the electrons and holes combine to produce excitons, and these excitons emit light while transitioning from an excited state to a ground state.

SUMMARY

The following is a summary of subject matter described in detail herein. This summary is not intended to limit the protection scope of the claims.

An organic light emitting device including an anode, a cathode, and an emitting layer disposed between the anode and the cathode, wherein, the emitting layer includes a host material and a dopant material doped in the host material; the host material and the dopant material satisfy:

$|HOMO_{Dopant}| < |HOMO_{Host}|, |LUMO_{Dopant}| \leq |LUMO_{Host}|$;

wherein, $HOMO_{Dopant}$ is a highest occupied molecular orbit (HOMO) energy level of the dopant material, $HOMO_{Host}$ is a HOMO energy level of the host material, $LUMO_{Dopant}$ is a lowest unoccupied molecular orbital (LUMO) energy level of the dopant material, and $LUMO_{Host}$ is a LUMO energy level of the host material.

In an exemplary embodiment, a hole block layer is further disposed between the emitting layer and the cathode, and the host material, the dopant material, and the hole block layer satisfy:

$|HOMO_{HBL} - HOMO_{Host}| \geq 20.5eV$, wherein, $HOMO_{HBL}$ is a HOMO energy level of the hole block layer.

In an exemplary embodiment, the dopant material and the hole block layer may satisfy:

$|HOMO_{HBL} - HOMO_{Dopant}| 0.9eV$.

In an exemplary embodiment, the host material and the hole block layer may satisfy:

$E_{HBL} \geq E_{Host}$, wherein, $E_{HBL}$ is an electron mobility of the hole block layer, and $E_{Host}$ is an electron mobility of the host material.

In an exemplary embodiment, the electron mobility of the hole block layer, $E_{HBL}$, is $10^{-5}$ cm$^2$/Vs to $10^{-8}$ cm$^2$/Vs, and the electron mobility of the host material, $E_{Host}$, is $10^{-6}$ cm$^2$/Vs to $10^{-8}$ cm$^2$/Vs.

In an exemplary embodiment, the host material and the hole block layer may satisfy:

$LUMO_{Host} > |LUMO_{HBL}|$, wherein, $LUMO_{HBL}$ is a LUMO energy level of the hole block layer.

In an exemplary embodiment, the dopant material and the hole block layer material may satisfy:

$T1_{HBL} > T1_{Dopant}$, wherein, $T1_{HBL}$ is a lowest triplet energy of the hole block layer and $T1_{Dopant}$ is a lowest triplet energy of the dopant material.

In an exemplary embodiment, a hole transport layer and an electron block layer are further disposed between the anode and the emitting layer, and the hole transport layer and the electron block layer satisfy:

$|HOMO_{HTL} - HOMO_{EBL}| < 0.3eV$, wherein, $HOMO_HTL$ is a HOMO energy level of the hole transport layer and $HOMO_EBL$ is a HOMO energy level of the electron block layer.

In an exemplary embodiment, the electron block layer and the host material satisfy:

$0.2eV < |HOMO_{EBL} - HOMO_{Host}| < 0.5eV$.

In an exemplary embodiment, the hole transport layer and the electron block layer satisfy:

$EK_{HTL} > EK_{EBL}$, wherein, $EK_{HTL}$ is a hole mobility of the hole transport layer and $EK_{EBL}$ is a hole mobility of the electron block layer.

In an exemplary embodiment, the hole mobility of the hole transport layer is $10^{-4}$ cm$^2$/Vs to $10^{-5}$ cm$^2$/Vs, and the hole mobility of the electron block layer is $10^{-5}$ cm$^2$/Vs to $10^{-7}$ cm$^2$/Vs.

In an exemplary embodiment, the host material includes anthracene derivatives, 9,10-(2-naphthyl)anthracene or 2-methyl-9,10-(2-naphthyl)anthracene.

In an exemplary embodiment, the host material includes one or more of the following compounds having the following structural formulas.

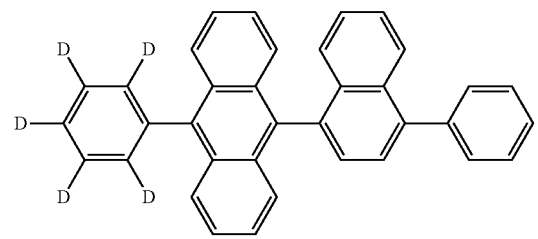

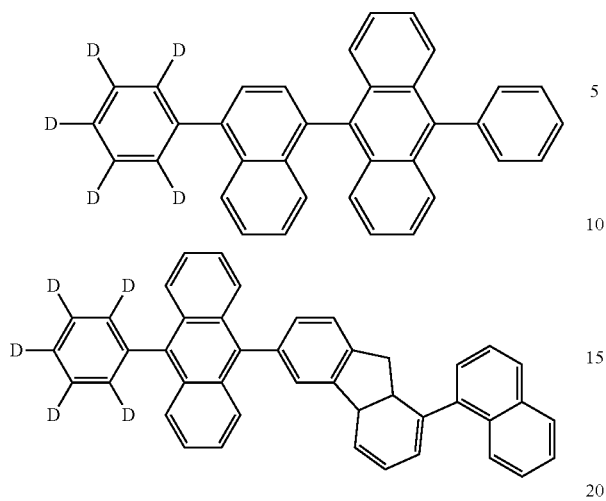

wherein D is tritium.

In an exemplary embodiment, the dopant material includes a compound having the following structural formula.

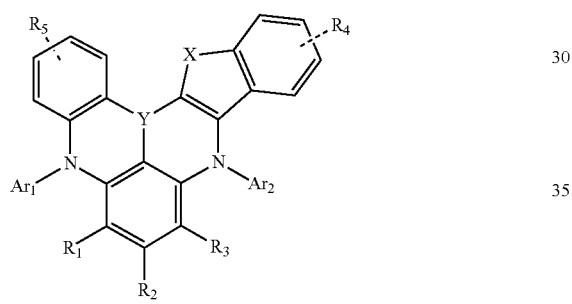

X is oxygen (O) or sulfur (S); Y is N-R7, B, P; R1 to R3 are hydrogen, deuterium, fluorine, C1-C4 alkyl, C3-C10 cycloalkyl, C1-C30 alkylsilyl, or C6-C10 arylsilyl; R4 and R5 are hydrogen, deuterium, fluorine, C1-C4 alkyl, C3-C10 cycloalkyl, C1-C30 alkylsilyl, or C6-C30 arylsilyl, substituted or unsubstituted C6-C30 aryl or heteroaryl; Ar and $Ar_2$ are substituted or unsubstituted C6-C30 aryl or heteroaryl; and R1 to R3 are the same or different.

In an exemplary embodiment, the dopant material includes one or more of the following compounds having the following structural formulas.

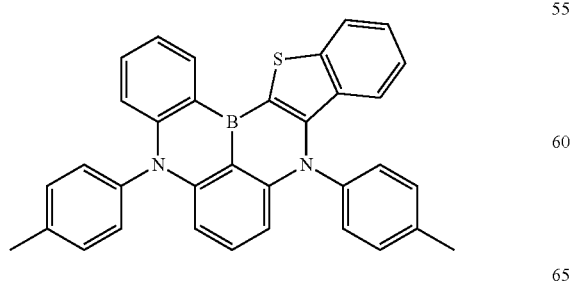

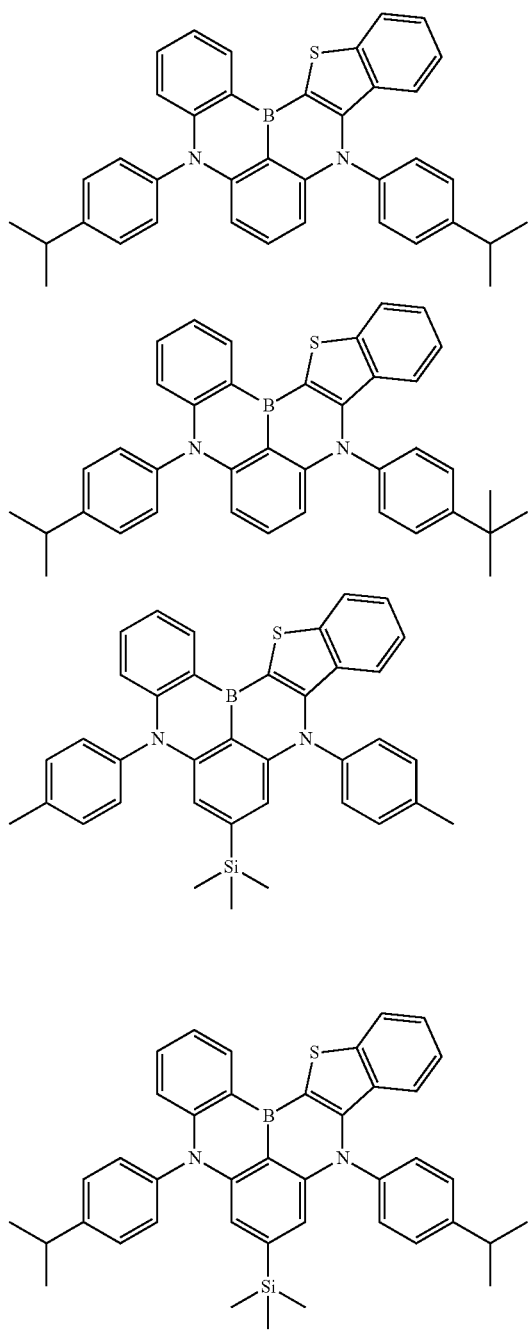

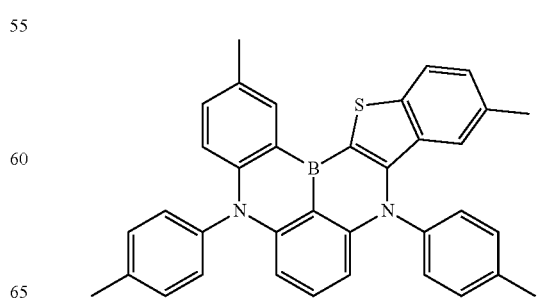

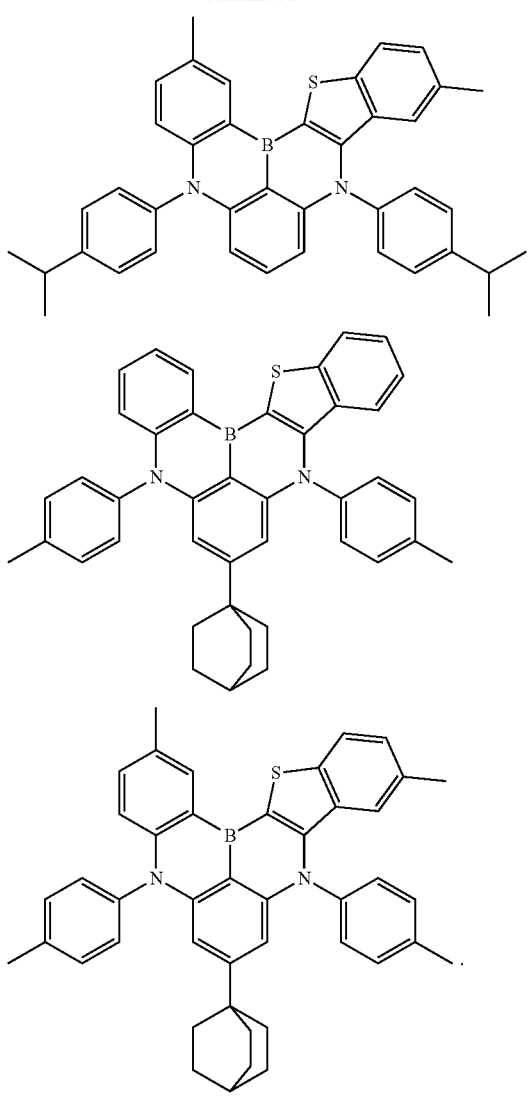

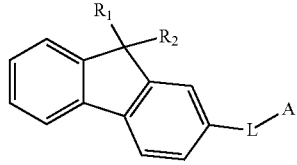

In an exemplary embodiment, the hole block layer includes, but is not limited to, a compound having the following structural formula.

L is substituted or unsubstituted C6-C30 aryl or heteroaryl; A is a substituted or unsubstituted nitrogen-containing aromatic heterocyclic which contains at least one nitrogen atom; R1 and R2 are methyl or aryl; R1 and R2 are the same or different.

In an exemplary embodiment, the hole block layer includes one or more of compounds having the following structural formula.

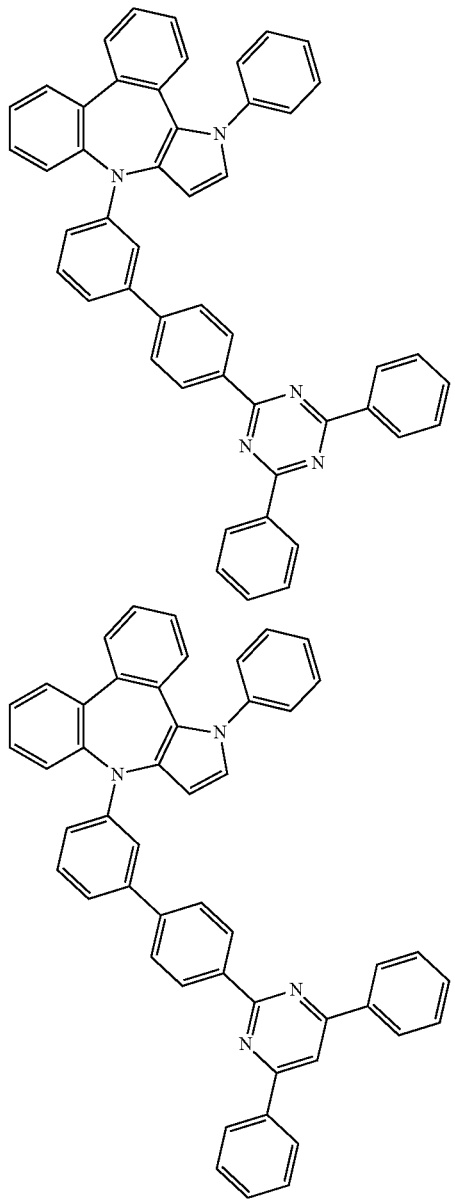

In an exemplary embodiment, wherein the hole block layer includes, but is not limited to, a compound having a structure represented by the following formula.

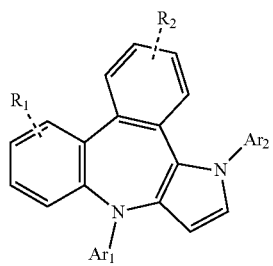

R1 and R2 are hydrogen, deuterium, and fluorine, C1-C4 alkyl, C3-C10 cycloalkyl, C1-C30 alkylsilyl, or C6-C10 arylsilyl; $Ar_1$ and $Ar_2$ are substituted or unsubstituted C6-C30 aryl or heteroaryl, one of which is heteroaryl containing at least one nitrogen; R1 and R2 are the same or different; $Ar_1$ and $Ar_2$ are different.

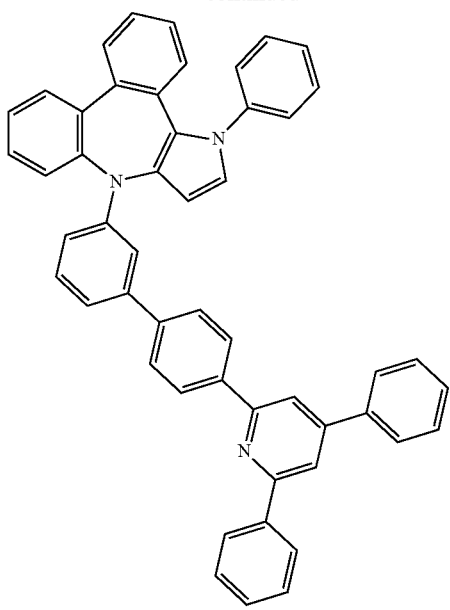
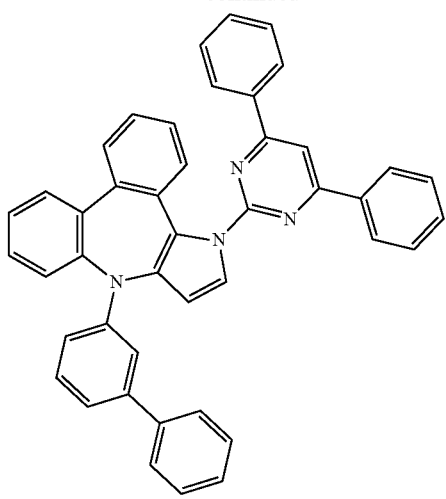
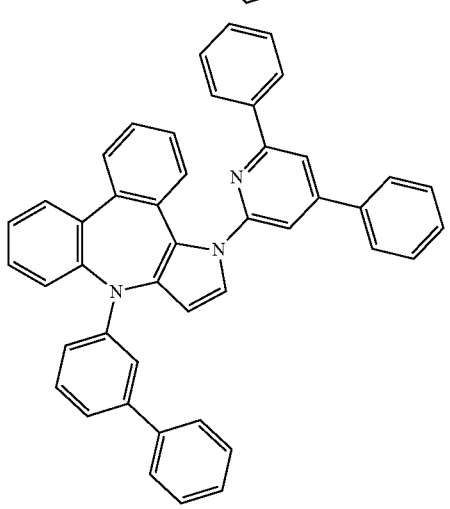
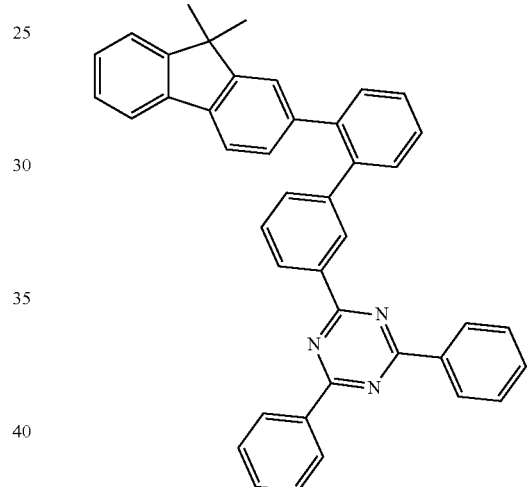
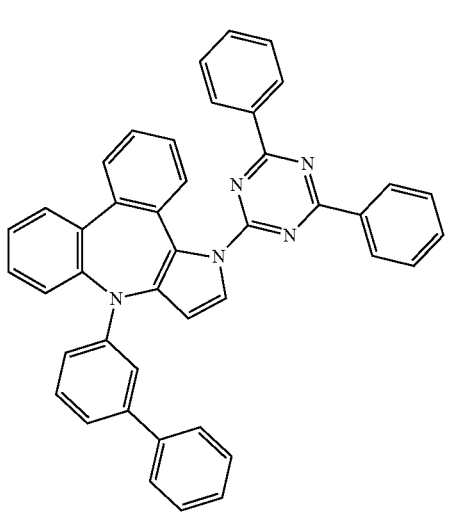
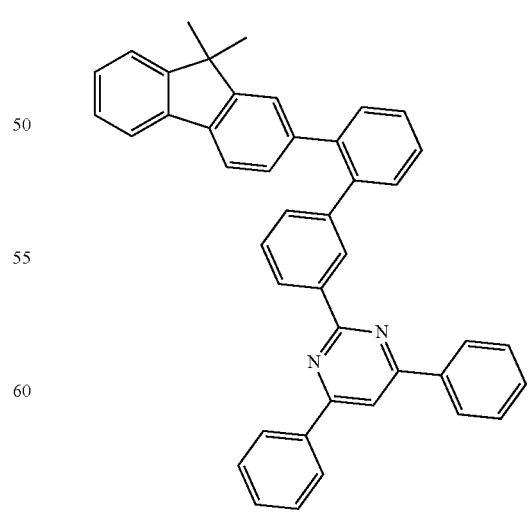

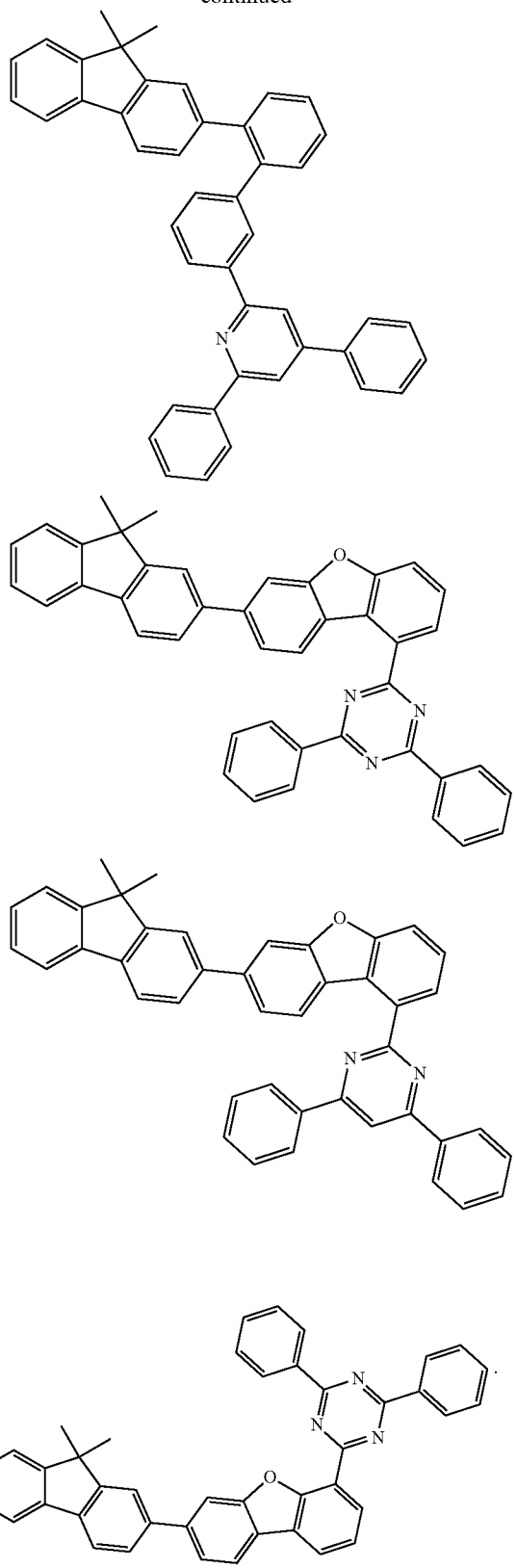

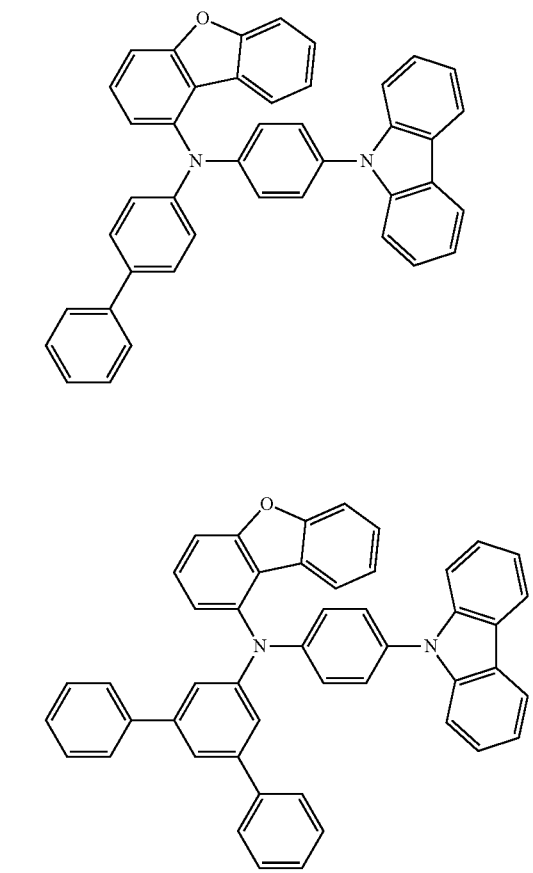

L1-L3 are single bond and C6-C15 aryl; $Ar_1$, $Ar_2$ are substituted or unsubstituted C6-C40 aryl, arylamino, or fluorenyl, $Ar_1$ and $Ar_2$ are different groups.

In an exemplary embodiment, a material of the electron block layer includes one or more of compounds having the following structural formulas.

In an exemplary embodiment, the material of the electron block layer includes, but is not limited to, any one of compounds having the following structural formulas.

-continued
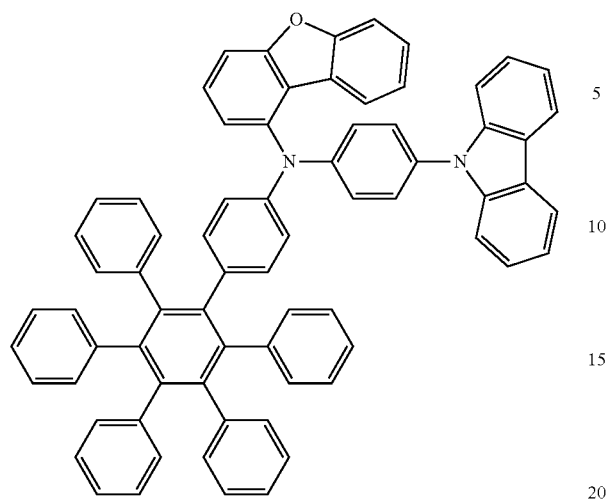
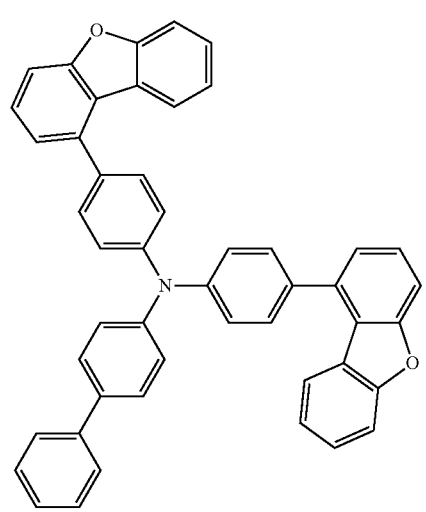
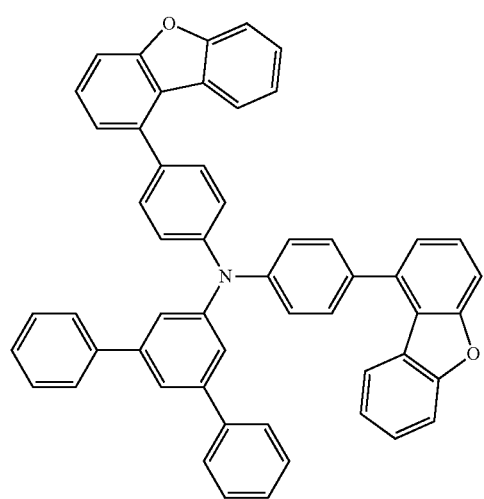
-continued
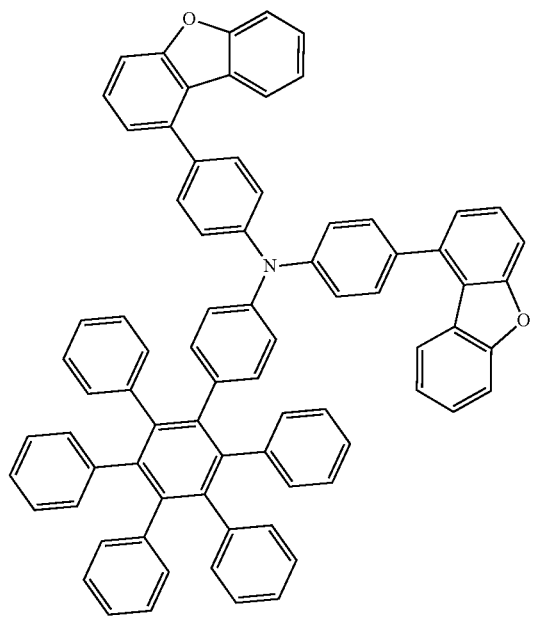
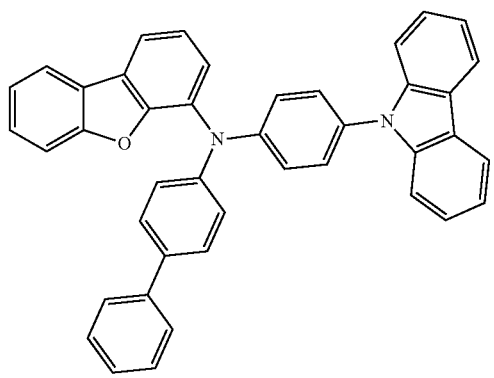
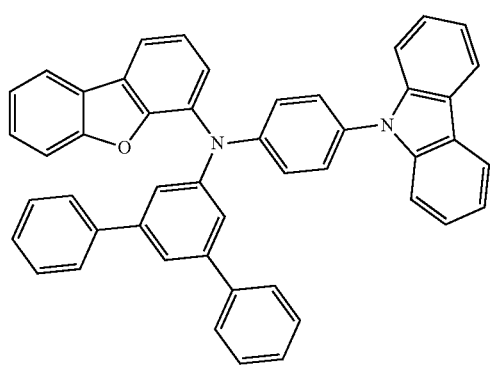

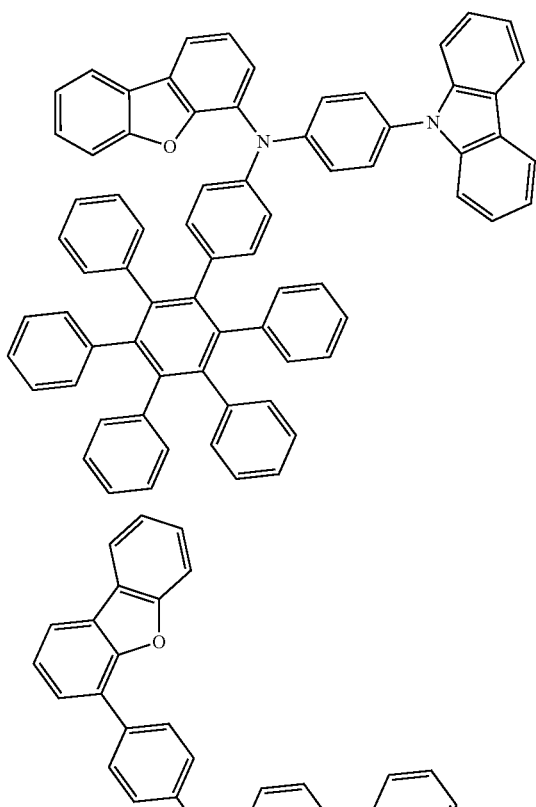
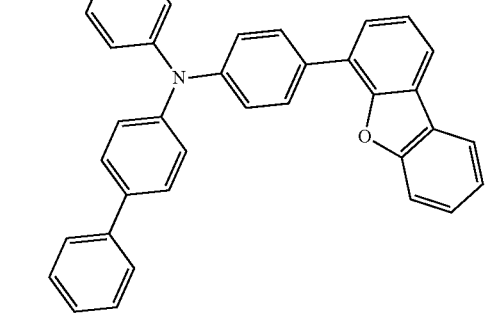
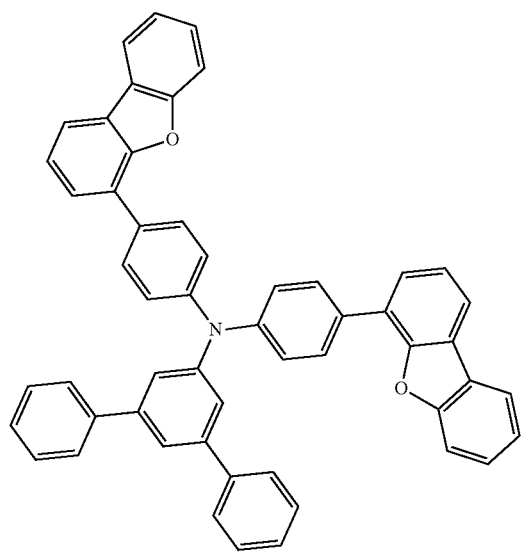
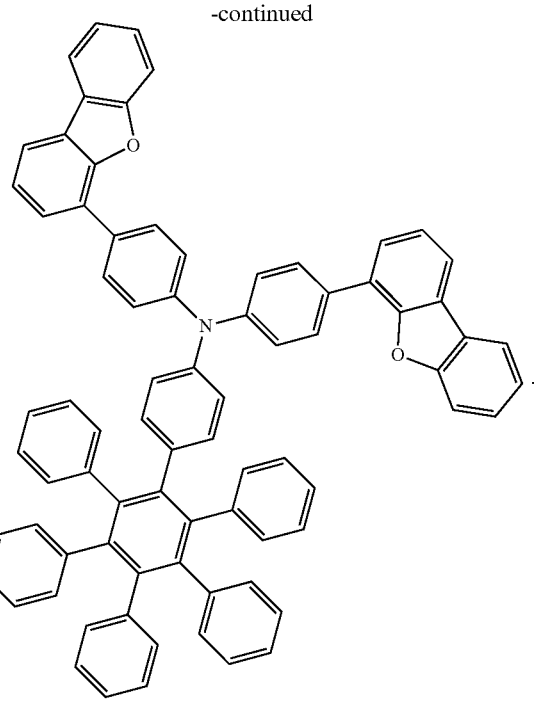
In an exemplary embodiment, one of $Ar_1$ and $Ar_2$ is a substituent having the following structural formula.
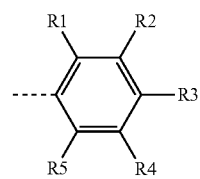
R1-R5 are hydrogen, deuterium, alkyl, cycloalkyl, or C6-C36 aryl.
In an exemplary embodiment, one of $Ar_1$ and $Ar_2$ is a substituent having the following structural formula.
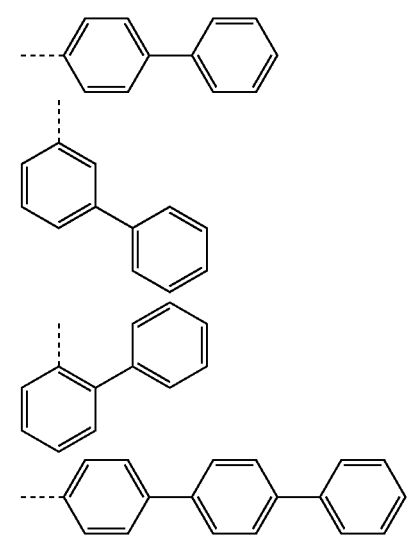

-continued

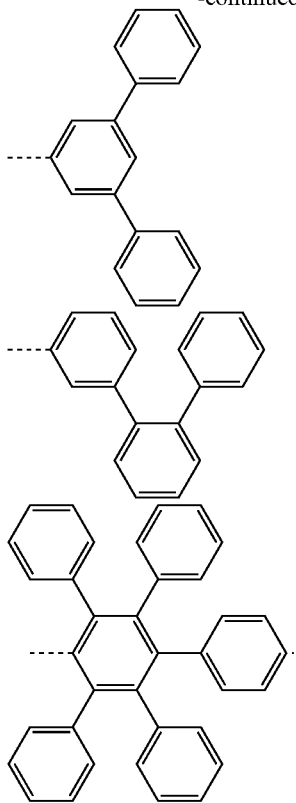

A display apparatus includes the aforementioned organic light emitting device.

Other aspects will become apparent upon reading and understanding accompanying drawings and the detailed description.

BRIEF DESCRIPTION OF DRAWINGS

The attached drawings are for providing a further understanding of technical schemes of the present disclosure and constitute a part of the description. They are for explaining the technical schemes of the present disclosure together with the embodiments of the present application and do not constitute a limitation on the technical schemes of the present disclosure. Shapes and sizes of various components in the drawings do not reflect true scales and are intended to illustrate schematically contents of the present disclosure only.

Figure 1:
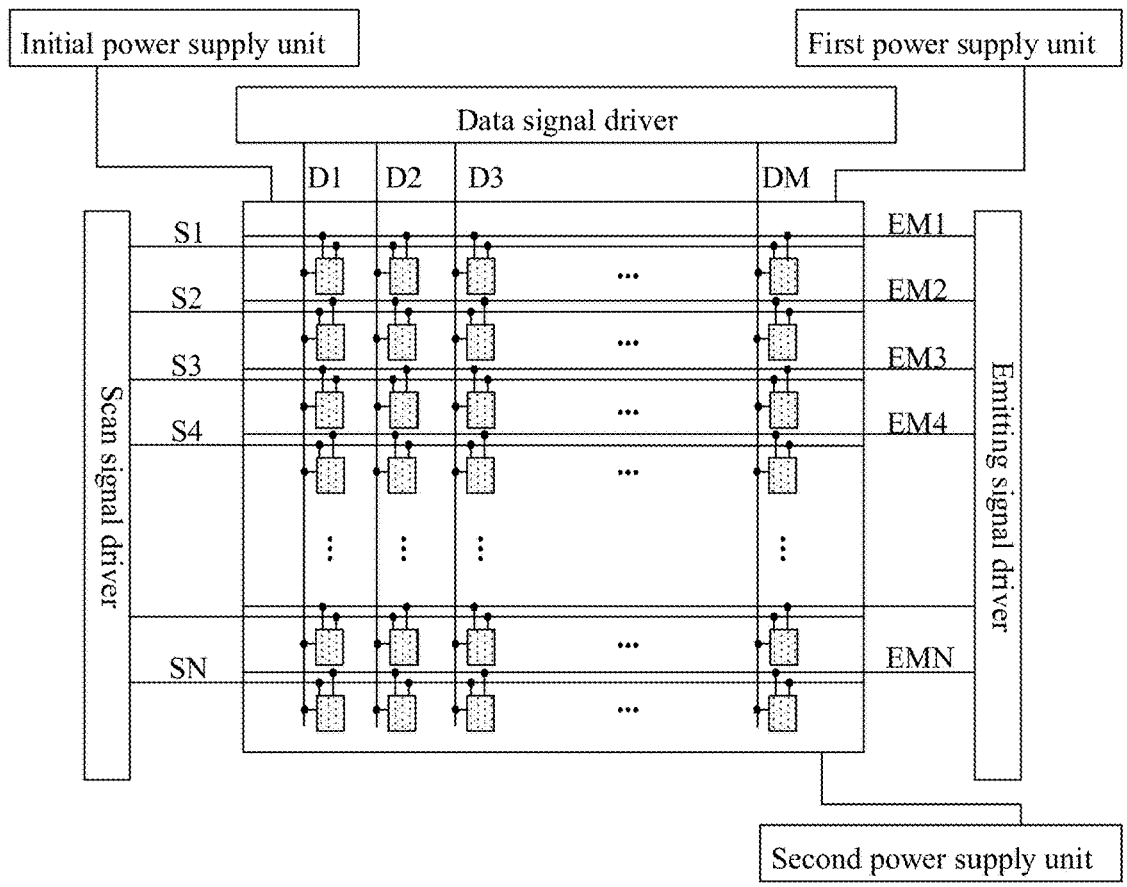
FIG. 1 is a schematic diagram of a structure of an OLED display apparatus.

DESCRIPTION OF REFERENCE SIGNS IS AS FOLLOWS 10-anode; 20-hole injection layer; 30-hole transport layer;
40-electron block layer; 50-emitting layer; 60-hole block layer;
70-electron transport layer; 80-electron injection layer; 90-cathode;
101-base substrate; 102-drive circuit layer; 103-emitting device;
104-encapsulation layer; 201-first insulating layer; 202-second insulating layer;
203-third insulating layer; 204-fourth insulating layer; 205-planarization layer;
210-drive transistor; 211-storage capacitor; 301-anode;
302-pixel define layer; 303-organic emitting layer; 304-cathode;
401-first encapsulation layer; 402-second encapsulation layer; 403-third encapsulation layer.

DETAILED DESCRIPTION

The embodiments in the present disclosure may be implemented in a plurality of different ways. A person of ordinary skills in the art will readily understand the fact that implementations and contents may be transformed into a variety of forms without departing from the spirit and scope of the present disclosure. Therefore, the present disclosure should not be construed as being limited only to what is described in the following embodiments. The embodiments and features in the embodiments in the present disclosure may be combined randomly if there is no conflict.

In the drawings, a size of a constituent element, a thickness of a layer or a region of the layer may be sometimes exaggerated for clarity. Therefore, any implementation of the present disclosure is not necessarily limited to sizes shown in the drawings, and shapes and sizes of components in the drawings do not reflect true proportions. In addition, the drawings schematically show ideal examples, and any implementation of the present disclosure is not limited to the shapes or values shown in the drawings.

In the present disclosure, the "first", "second", "third" and other ordinal numbers are used to avoid confusion of constituent elements, but not to limit in quantity.

In the present disclosure, for sake of convenience, wordings and sentences indicating orientations or positional relationships such as "central", "upper", "lower", "front", "rear", "vertical", "horizontal", "top", "bottom", "inner", "outer" and the like describe positional relationships of constituent elements with reference to the drawings, which are only for ease of describing embodiments and simplifying description, rather than indicating or implying that the apparatus or element referred to must have a specific orientation, or must be constructed and operated in a specific orientation, and therefore may not be construed as limitations on the present disclosure. The positional relationships of the constituent elements may be appropriately changed according to a direction in which each constituent element is described. Therefore, it is not limited to the words and sentences described in the present disclosure, and may be changed appropriately according to situations.

In the present disclosure, the terms "installed", "connected", and "coupled" shall be broadly understood unless otherwise explicitly specified and defined. For example, a connection may be a fixed connection, or a detachable connection, or an integrated connection; it may be a mechanical connection, or an electrical connection; it may be a direct connection, or an indirect connection through middleware, or an internal connection between two elements. Those of ordinary skills in the art may understand specific meanings of the above terms in the present disclosure according to situations.

In the present disclosure, a transistor refers to an element that includes at least three terminals: a gate electrode, a drain electrode, and a source electrode. The transistor has a channel region between the drain electrode (or referred to as a drain electrode terminal, a drain region, or a drain electrode) and the source electrode (or referred to as a source electrode terminal, a source region, or a source electrode), and a current may flow through the drain electrode, the channel region, and the source electrode. In the present disclosure, the channel region refers to a region through which a current mainly flows.

In the present disclosure, a first electrode may be a drain electrode and a second electrode may be a source electrode, or a first electrode may be a source electrode and a second electrode may be a drain electrode. In a situation where transistors with opposite polarities are used or a direction of a current is changed in an operation of a circuit, a function of the "source electrode" and a function of the "drain electrode" may sometimes be interchangeable. Therefore, the "source electrode" and the "drain electrode" may be interchangeable in the present disclosure.

In the present disclosure, an "electrical connection" includes a case where constituent elements are connected via an element with some kind of electrical function. The "element with some kind of electrical function" is not particularly limited as long as it may transmit and receive electrical signals among connected constituent elements. An "element some kind of electrical function" may be, for example, an electrode or wiring, a switch element such as a transistor, or other functional elements such as a resistor, an inductor, or a capacitor.

In the present disclosure, "parallel" refers to a state in which an angle formed by two straight lines is −10° or more and 10° or less, and thus also includes a state in which an angle is −5° or more and 5° or less. In addition, "perpendicular" refers to a state in which an angle formed by two straight lines is 80° or more and 100° or less, and thus also includes a state in which an angle is 850 or more and 950 or less.

In the present disclosure, a "film" and a "layer" are interchangeable. For example, sometimes a "conductive layer" may be replaced by a "conductive film". Similarly, an "insulating film" may sometimes be replaced by an "insulating layer".

The wording "about" in the present disclosure means that a limit is not strictly set, and a value within a range of process and measurement errors is allowed.

FIG. 1 is a schematic diagram of a structure of an OLED display apparatus. As shown in FIG. 1, the OLED display apparatus may include a scan signal driver, a data signal driver, an emitting signal driver, an OLED display substrate, a first power supply unit, a second power supply unit, and an initial power supply unit. In an exemplary embodiment, an OLED display substrate at least includes a plurality of scan signal lines (S1 to SN), a plurality of data signal lines (D1 to DM) and a plurality of emitting signal lines (EM1 to EMN); the scan signal driver is configured to sequentially supply scan signals to the plurality of scan signal lines (S1 to SN), the data signal driver is configured to supply data signals to the plurality of data signal lines (D1 to DM), and the emitting signal driver is configured to sequentially supply emitting control signals to the plurality of emitting signal lines (EM1 to EMN). In an exemplary embodiment, the plurality of scan signal lines and the plurality of emitting signal lines extend along a horizontal direction, and the plurality of data signal lines extend along a vertical direction. The display apparatus includes a plurality of sub-pixels. One sub-pixel includes a pixel drive circuit and an emitting device. The pixel drive circuit is connected to a scan signal line, an emitting signal line, and a data signal line. The pixel drive circuit is configured to receive data voltage transmitted by the data signal line under control of the scan signal line and the emitting signal line, and output a corresponding current to the emitting device, the emitting device is connected to the pixel drive circuit, and the emitting device is configured to emit light with corresponding brightness in response to the current output by the pixel drive circuit. The first power supply unit, the second power supply unit, and the initial power supply unit are respectively configured to supply a first power supply voltage, a second power supply voltage, and an initial power supply voltage to the pixel drive circuit through a first power supply line, a second power supply line, and an initial signal line.

Figure 2:
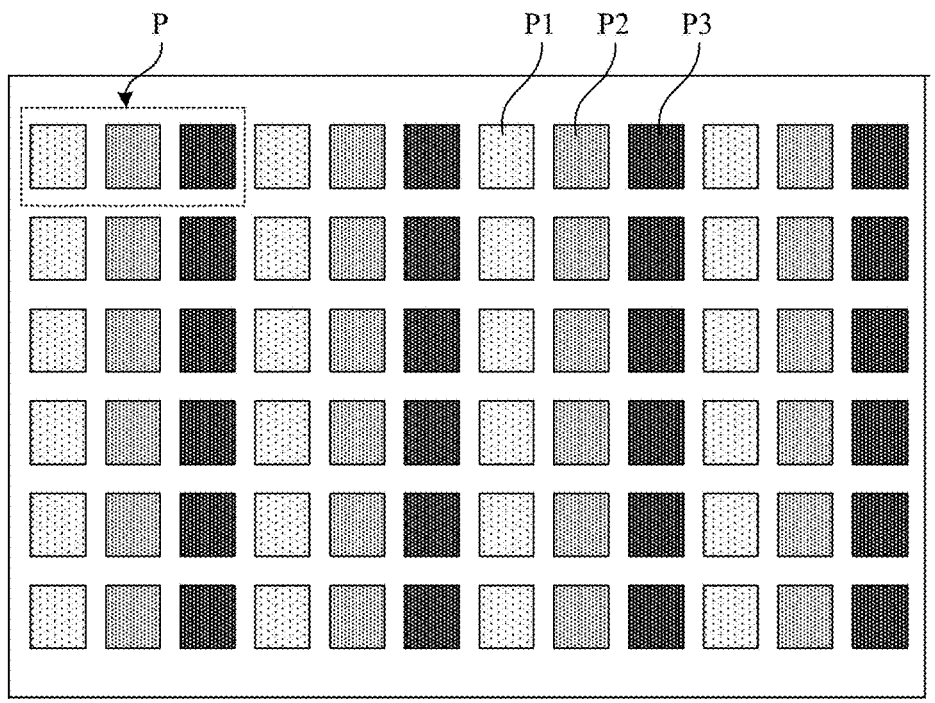
FIG. 2 is a schematic diagram of a planar structure of a display substrate.

FIG. 2 is a schematic diagram of a planar structure of a display substrate. As shown in FIG. 2, a display region may include a plurality of pixel units P arranged in a matrix, at least one of the plurality of pixel units P includes a first sub-pixel P1 emitting light of a first color, a second sub-pixel P2 emitting light of a second color, and a third sub-pixel P3 emitting light of a third color. The first sub-pixel P1, the second sub-pixel P2, and the third sub-pixel P3 each include a pixel drive circuit and an emitting device. In an exemplary embodiment, a pixel unit P may include red (R), green (G), and blue (B) sub-pixels, or may include red, green, blue, and white (W) sub-pixels, which is not limited in the present disclosure. In an exemplary embodiment, a shape of a sub-pixel in a pixel unit may be rectangular, diamond, pentagonal, or hexagonal. When a pixel unit includes three sub-pixels, the three sub-pixels may be arranged in a manner to stand side by side horizontally, in a manner to stand side by side vertically, or in a pyramid manner with two units sitting at the bottom and one unit placed on top. When a pixel unit includes four sub-pixels, the four sub-pixels may be arranged in a manner to stand side by side horizontally, in a manner to stand side by side vertically, or in a manner to form a square, which is not limited in the present disclosure.

Figure 3:
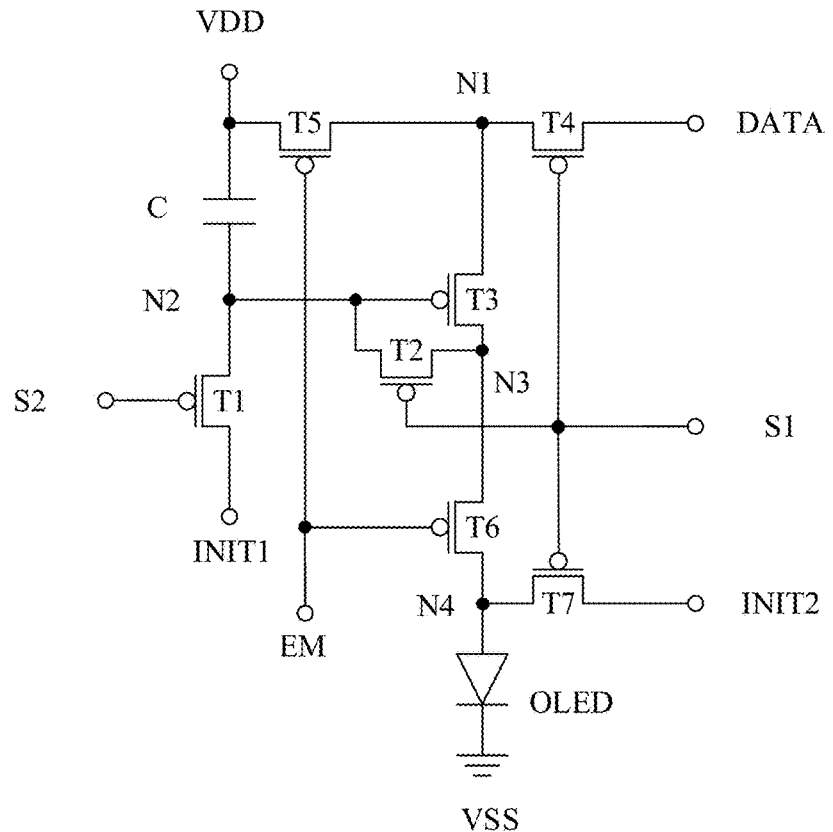
FIG. 3 is an equivalent circuit diagram of a pixel drive circuit.

In an exemplary implementation, a pixel drive circuit may have a structure of 3T1C, 4T1C, 5T1C, 5T2C, 6TIC, or 7TIC. FIG. 3 is an equivalent circuit diagram of a pixel drive circuit. As shown in FIG. 3, the pixel drive circuit may include seven switch transistors (a first transistor T1 to a seventh transistor T7), a storage capacitor C, and eight signal lines (a data signal line DATA, a first scan signal line S1, a second scan signal line S2, a first initial signal line INIT1, a second initial signal line INIT2, a first power supply line VSS, a second power supply line VDD, and an emitting signal line EM). The first initial signal line INIT1 and the second initial signal line INIT2 may be the same signal line.

In an exemplary implementation, a control electrode of the first transistor T1 is connected to the second scan signal line S2, a first electrode of the first transistor T1 is connected to the first initial signal line INIT1, and a second electrode of the first transistor is connected to a second node N2. A control electrode of the second transistor T2 is connected to the first scan signal line S1, a first electrode of the second transistor T2 is connected to the second node N2, and a second electrode of the second transistor T2 is connected to a third node N3. A control electrode of the third transistor T3 is connected to the second node N2, a first electrode of the third transistor T3 is connected to the first node N1, and a second electrode of the third transistor T3 is connected to the third node N3. A control electrode of the fourth transistor T4 is connected to the first scan signal line S1, a first electrode of the fourth transistor T4 is connected to the data signal line DATA, and a second electrode of the fourth transistor T4 is connected to the first node N1. A control electrode of the fifth transistor T5 is connected to the emitting signal line EM, a first electrode of the fifth transistor T5 is connected to the second power supply line VDD, and a second electrode of the fifth transistor T5 is connected to the first node N1. A control electrode of the sixth transistor T6 is connected to the light emitting signal line EM, a first electrode of the sixth transistor T6 is connected to the third node N3, and a second electrode of the sixth transistor T6 is connected to a first electrode of the emitting device. A control electrode of the seventh transistor T7 is connected to the first scan signal line S1, a first electrode of the seventh transistor T7 is connected to the second initial signal line INIT2, and a second electrode of the seventh transistor T7 is connected to the first electrode of the emitting device. A first terminal of the storage capacitor C is connected to the second power supply line VDD, and a second terminal of the storage capacitor C is connected to the second node N2.

In an exemplary implementation, the first transistor T1 to the seventh transistor T7 may be P-type transistors, or may be N-type transistors. Adopting transistors of the same type in a pixel drive circuit may simplify a process flow, reduce process difficulties of a display panel, and improve a product yield. In some possible implementations, the first transistor T1 to the seventh transistor T7 may include P-type transistors and N-type transistors.

In an exemplary implementation, a second electrode of the light emitting device is connected to the first power supply line VSS. A signal of the first power supply line VSS is a low level signal and a signal of the second power supply line VDD is a high level signal that is continuously supplied. The first scan signal line Si is a scan signal line in a pixel drive circuit of a present display row, and the second scan signal line S2 is a scan signal line in a pixel drive circuit of a previous display row. That is, for an n-th display row, the first scan signal line S1 is S(n), the second scan signal line S2 is S(n-1), the second scan signal line S2 of the present display row and the first scan signal line Si in the pixel drive circuit of the previous display row are the same signal line, which may reduce signal lines of the display panel and realize a narrow frame of the display panel.

Figure 4:
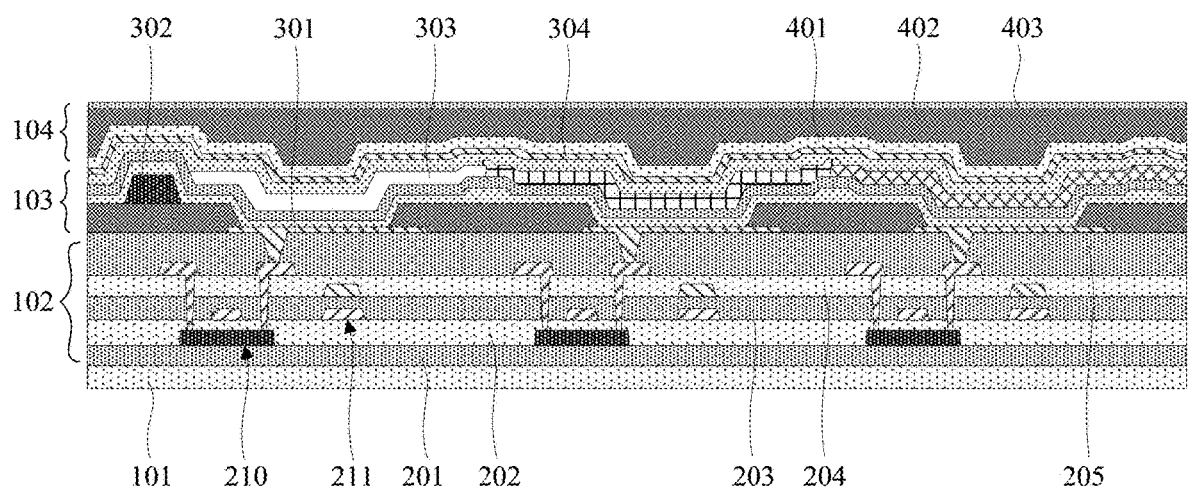
FIG. 4 is a schematic diagram of a sectional structure of a display substrate.

FIG. 4 is a schematic diagram of a sectional structure of a display substrate, showing a structure of three sub-pixels in an OLED display substrate. As shown in FIG. 4, on a plane perpendicular to the display substrate, the display substrate may include a drive circuit layer 102 disposed on a substrate 101, an emitting device 103 disposed on a side of the drive circuit layer 102 away from the substrate 101, and an encapsulation layer 104 disposed on a side of the emitting device 103 away from the substrate 101. In some possible implementations, the display substrate may include other film layers, such as spacer posts, etc., which is not limited in the present disclosure.

In an exemplary implementation, the substrate may be a flexible substrate, or may be a rigid substrate. The flexible substrate may include a first flexible material layer, a first inorganic material layer, a semiconductor layer, a second flexible material layer, and a second inorganic material layer which are stacked, materials of the first flexible material layer and the second flexible material layer may be polyimide (PI), polyethylene terephthalate (PET), or a polymer soft film with surface treatment and the like; materials of the first inorganic material layer and the second inorganic material layer may be silicon nitride (SiNx) or silicon oxide (SiOx), etc., for improving water-resistance and oxygen-resistance of the substrate; and a material of the semiconductor layer may be amorphous silicon (a-si).

In an exemplary embodiment, the drive circuit layer 102 of each sub-pixel may include a plurality of transistors and a storage capacitor constituting a pixel drive circuit, an example of which is illustrated in FIG. 3 where each sub-pixel includes a drive transistor and a storage capacitor. In some possible implementations, the drive circuit layer 102 of each sub-pixel may include: a first insulating layer 201 disposed on the substrate; an active layer disposed on the first insulating layer; a second insulating layer 202 covering the active layer; a gate electrode and a first capacitor electrode that are disposed on the second insulating layer 202; a third insulating layer 203 covering the gate electrode and the first capacitor electrode; a second capacitor electrode disposed on the third insulating layer 203; a fourth insulating layer 204 covering the second capacitor electrode, wherein the second insulating layer 202, the third insulating layer 203, and the fourth insulating layer 204 are provided with via holes exposing the active layer; a source electrode and a drain electrode that are disposed on the fourth insulating layer 204, wherein the source electrode and the drain electrode are respectively connected to the active layer through via holes; and a planarization layer 205 covering the aforementioned structure, wherein the planarization layer 205 is provided with a via hole exposing the drain electrode. The active layer, the gate electrode, the source electrode, and the drain electrode form a drive transistor 210. The first capacitor electrode and the second capacitor electrode form a storage capacitor 211.

In an exemplary embodiment, the emitting device 103 may include an anode 301, a pixel define layer 302, an organic emitting layer 303 and a cathode 304. The anode 301 is disposed on the planarization layer 205, and is connected to the drain electrode of the drive transistor 210 through a via hole disposed on the planarization layer 205. The pixel define layer 302 is disposed on the anode 301 and the planarization layer 205, and the pixel define layer 302 is provided with a pixel opening exposing the anode 301. The organic emitting layer 303 is at least partially disposed in the pixel opening, and is connected to the anode 301. The cathode 304 is disposed on the organic emitting layer 303, and is connected to the organic emitting layer 303. The organic emitting layer 303 emits light of corresponding colors under drive of the anode 301 and the cathode 304.

In an exemplary embodiment, an encapsulation layer 104 may include a first encapsulation layer 401, a second encapsulation layer 402, and a third encapsulation layer 403 that are stacked; the first encapsulation layer 401 and the third encapsulation layer 403 may be made of an inorganic material, and the second encapsulation layer 402 may be made of an organic material; the second encapsulation layer 402 is disposed between the first encapsulation layer 401 and the third encapsulation layer 403 to ensure that external vapor cannot enter into the emitting device 103.

In an exemplary embodiment, an organic emitting layer of an OLED emitting element may include an Emitting Layer (EML), and one or more film layers of a Hole Injection Layer (HIL), a Hole Transport Layer (HTL), a Hole Block Layer (HBL), an Electron Block Layer (EBL), an Electron Injection Layer (EIL), and an Electron Transport Layer (ETL). Driven by voltages of an anode and a cathode, light is emitted using emitting characteristics of an organic material according to a required gray scale.

In an exemplary embodiment, emitting layers of OLED emitting elements of different colors are different. For example, a red emitting element includes a red emitting layer, a green emitting element includes a green emitting layer, and a blue emitting element includes a blue emitting layer. In order to reduce process difficulties and improve a yield, a common layer may be used for a hole injection layer and a hole transport layer on a side of an emitting layer, and a common layer may be used for an electron injection layer and an electron transport layer on the other side of the emitting layer. In an exemplary embodiment, any one or more layers of the hole injection layer, the hole transport layer, the electron injection layer, and the electron transport layer may be manufactured by one process (one evaporation process or one ink-jet printing process), but isolation is realized by means of a surface height difference of formed film layers or by means of a surface treatment. For example, any one or more layers of the hole injection layer, the hole transport layer, the electron injection layer, and the electron transport layer corresponding to adjacent sub-pixels may be isolated. In an exemplary embodiment, the organic emitting layer may be manufactured by evaporation using a Fine Metal Mask (FMM) or an Open Mask, or by an ink-jet process.

In an OLED structure, a blue emitting element has a short service life, which leads to white balance color drift after long-term use, and visual phenomenon such as color pink when a white screen is on, which restricts an application of OLED display, and may not be applied to an equipment with a long service life. Although a research on new blue emitting layer materials may improve a service life of blue emitting elements, after years of development, a cost of improving a service life from a direction of materials is getting increasingly high, and a progress potential thereof is getting increasingly small.

Figure 5:
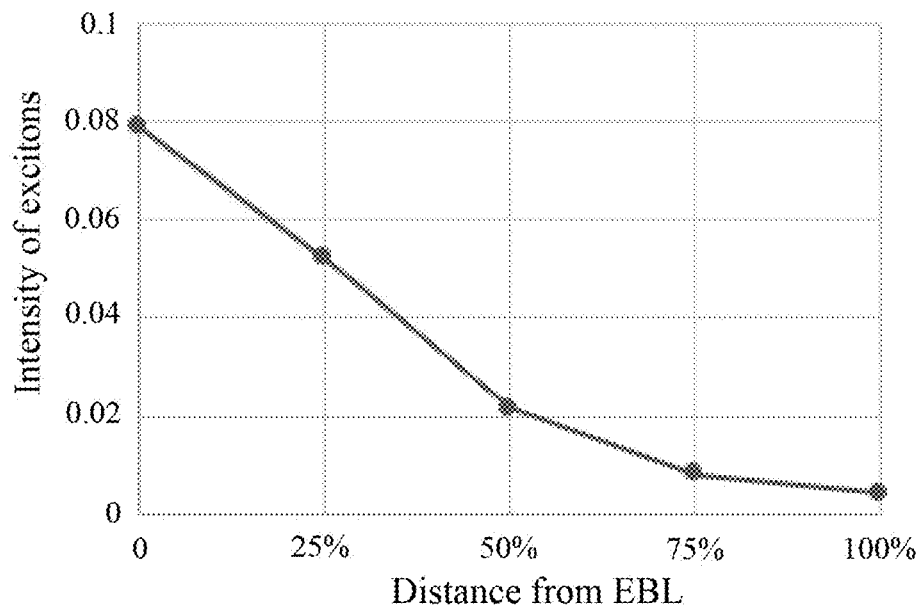
FIG. 5 is a schematic diagram of a distribution of excitons in an emitting layer.

The research shows that performance of OLED emitting elements depends on properties of materials and collocation structures of devices. The properties of materials are related to energy level, mobility, stability, and material fluorescence quantum yield (PLQY), etc. The collocation structure of devices involves energy level collocations of adjacent layers, distributions of excitons, injections of electrons and holes, and accumulations of electrons and holes, etc. A further research shows that materials which are more prone to degradation in OLED emitting elements include an electron block layer (also called a hole auxiliary layer). There is a large energy level barrier between the electron block layer and a host material of the blue emitting layer, which leads to an accumulation of holes at an interface of the electron block layer and the emitting layer, and makes the emitting composite region close to the interface. FIG. 5 is a schematic diagram of a distribution of excitons in an emitting layer. As shown in FIG. 5, excitons in the emitting layer are mainly concentrated at 0% of the interface of the electron block layer and the emitting layer, so that excessive electrons are accumulated at the interface.

Generally, a material itself of the electron block layer is generally a material of an electron-abundance system (containing an aromatic amine structure), and excessive electrons will have a repulsive force with abundance electrons of the electron block layer itself, the repulsive force will cause a distortion of the 6 bond of benzene rings on aniline, and a result of the distortion of the 6 bond caused by an external force is bond fracture, resulting in material defects and rapid device life decay. Therefore, the defects caused by bond fracture are basis of material and device life decay (i.e., material deterioration).

Figure 6:
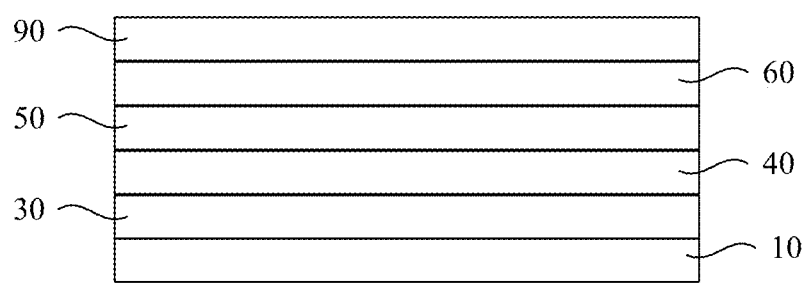
FIG. 6 is a schematic diagram of an OLED structure according to an exemplary embodiment of the present disclosure.

FIG. 6 is a schematic diagram of an OLED structure according to an exemplary embodiment of the present disclosure. As shown in FIG. 6, the OLED includes an anode 10, a cathode 90, and an organic emitting layer disposed between the anode 10 and the cathode 90. In an exemplary embodiment, the organic light emitting layer may include a hole transport layer 30, an electron block layer 40, an emitting layer 50, and a hole block layer 60 which are stacked, the hole transport layer 30 and the electron block layer 40 are disposed between the anode 10 and the emitting layer 50, and the hole block layer 60 is disposed between the emitting layer 50 and the cathode 90. The hole transport layer 30 is disposed near the anode 10, and the electron block layer 40 is disposed near the emitting layer 50, that is, the hole transport layer 30 is disposed between the anode 10 and the electron block layer 40, and the electron block layer 40 is disposed between the hole transport layer 30 and the emitting layer 50. In an exemplary embodiment, the hole transport layer 30 is configured to realize directional and orderly controlled migration of injected holes, and the electron block layer 40 is configured to form a migration barrier for electrons and prevent electrons from migrating out of the emitting layer 50. The emitting layer 50 is configured to combine electrons and holes to emit light. The hole block layer 60 is configured to form a migration barrier for holes and prevent holes from migrating out of the emitting layer 50. In an exemplary embodiment, the emitting layer 50 includes a Host material and a Dopant material doped in the Host material.

Figure 7:
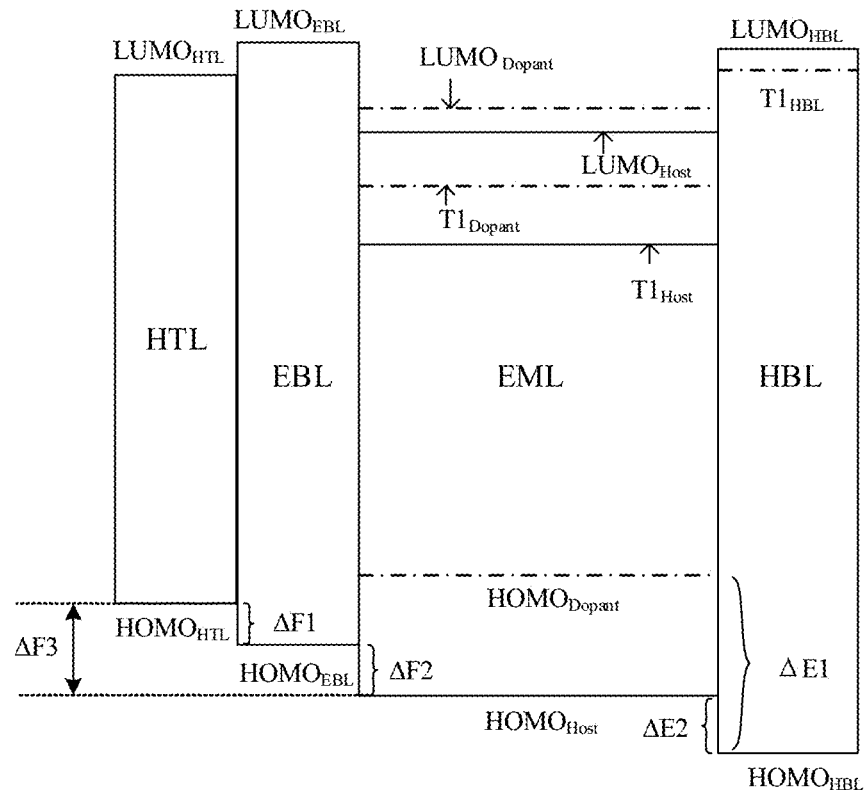
FIG. 7 is a schematic diagram of an energy level relationship of an OLED structure according to an exemplary embodiment of the present disclosure.

FIG. 7 is a schematic diagram of an energy level relationship of an OLED structure according to an exemplary embodiment of the present disclosure. As shown in FIG. 7, in an exemplary embodiment, a Highest Occupied Molecular Orbit (HOMO) energy level of a Dopant material of an emitting layer, $HOMO_{Dopant}$, is higher than a HOMO energy level of an electron block layer (EBL), $HOMO_{EBL}$; a HOMO energy level of a hole transport layer (HTL), $HOMO_{HTL}$, is higher than a HOMO energy level of an electron block layer (EBL), The HOMO energy level of an electron block layer (EBL), $HOMO_{EBL}$, is higher than a HOMO energy level of a Host material of the emitting Layer, $HOMO_{Host}$; the HOMO energy level of the Host material of the emitting Layer, $HOMO_{Host}$, is higher than a HOMO energy level of a hole block layer (HBL), $HOMO_{HBL}$. A Lowest Unoccupied Molecular Orbit (LUMO) energy level of the hole block layer (HBL), $LUMO_{HBL}$, is higher than a LUMO energy level of the Dopant material of the emitting Layer, $LOMO_{Dopant}$; the LUMO energy level of the Dopant material of the emitting Layer, $LUMO_{Dopant}$, is higher than a LUMO energy level of the Host material of the emitting Layer, $LUMO_{Host}$; a LUMO energy level of the electron block layer (EBL), $LUMO_{EBL}$ is higher than the LUMO energy level of the Dopant material of the emitting Layer, $LUMO_{Dopant}$; a LUMO energy level of the electron block layer (EBL), $LUMO_{EBL}$ is higher than a LUMO energy level of the hole transport layer (HTL), $LUMO_{HTL}$. In an exemplary embodiment, the LUMO energy level of the electron block layer (EBL), $LUMO_{EBL}$ is higher than a LUMO energy level of the hole block layer (HBL), $LUMO_{HBL}$. In an exemplary embodiment, a lowest triplet energy of the hole block layer (HBL), $T1_{HBL}$, is greater than a lowest triplet energy of the Dopant material of the emitting layer, $T1_{Dopant}$; and the lowest triplet energy of the Dopant material of the emitting layer, $T1_{Dopant}$ is greater than a lowest triplet energy of the Host material of the emitting layer $T1_{Host}$.

In an exemplary embodiment, the Host material of the emitting layer and the Dopant material of the emitting layer may satisfy:

$$|HOMO_{Dopant}|<|HOMO_{Host}|, |LUMO_{Dopant}| \leq \leq |LUMO_{Host}|.$$

In an exemplary embodiment, a HOMO energy level relationship and LUMO energy level relationship between the Host material of the emitting layer and the Dopant material of the emitting layer are set, which is conducive to effective energy transfer.

In an exemplary embodiment, the Host material of the emitting layer and the hole block layer may satisfy:

$$|HOMO_{HBL}-HOMO_{Host}|0.5eV, i.e., \Delta E2>0.5eV.$$

In an exemplary embodiment, a HOMO energy level relationship between the hole block layer and the Host material of the emitting layer is set, which is conducive to blocking of holes.

In an exemplary embodiment, the Dopant material of the emitting layer and the hole block layer may satisfy:

$$|HOMO_{HBL}-HOMO_{Dopant}|>0.9eV, i.e., \Delta E1>0.9eV.$$

In an exemplary embodiment, the Host material of the emitting layer and the hole block layer may satisfy:

$$|LUMO_{Host}|>|LUMO_{HBL}|.$$

In an exemplary embodiment, a LUMO energy level relationship between the Host material of the emitting layer and the hole block layer is set, which is conducive to transporting of electrons.

In an exemplary embodiment, the Dopant material of the emitting layer and the hole block layer may satisfy:

$$T1_{HBL} \geq T_{Dopant},$$

wherein $T1_{HBL}$ is a lowest triplet energy of the hole block layer and T1Dopant is a lowest triplet energy of the Dopant material of the emitting layer.

In an exemplary embodiment, a lowest triplet energy relationship between the Dopant material of the emitting layer and the hole block layer is set, which is beneficial for excitons to compositely emit light in the emitting layer.

In an exemplary embodiment, the hole transport layer and the electron block layer may satisfy:

$$|HOMO_{HTL}-HOMO_{EBL}|<0.3eV, i.e., \Delta F1<0.3eV;$$

$$0.2eV \leq |HOMO_{EBL}-HOMO_{Host}|<0.5eV, that\ is, 0.2eV<\Delta F2<0.5eV.$$

In an exemplary embodiment, setting a HOMO energy level relationship between the hole transport layer and the electron block layer, and a HOMO energy level relationship between the electron block layer and the Host material of the emitting layer is not only beneficial for holes to be transported to the emitting layer, but also may effectively reduce an energy level barrier $\Delta F3$ between the hole transport layer and the Host material of the emitting layer, and reduce a voltage of a device, wherein $$\Delta F3=\Delta F1+\Delta F2=|HOMO_{HTL}-HOMO_{Host}|.$$

In an exemplary embodiment, the Host material of the emitting layer and the hole block layer may satisfy:

$$E_{HBL}>E_{Host},$$

wherein $E_{HBL}$ is electron mobility of the hole block layer, and $E_{Host}$ is electron mobility of the Host material of the emitting layer.

In an exemplary embodiment, setting an electron mobility relationship between the hole block layer and the Host material of the emitting layer, is beneficial to increase a probability of electrons in the Host material of the emitting layer moving towards the hole block layer, beneficial to reduce an accumulation of electrons at an interface between the emitting layer and the electron block layer, slow down material deterioration of the electron block layer at the interface, and make an exciton composite region move towards a center of the emitting layer.

In an exemplary embodiment, the hole transport layer and the electron block layer may satisfy:

$$EK_{HTL}>EK_{EBL},$$

wherein $EK_{HTL}$ is hole mobility of the hole transport layer and $EK_{EBL}$ is hole mobility of the electron block layer.

In an exemplary embodiment, setting a hole mobility relationship between the hole transport layer and the electron block layer is beneficial to reduce an accumulation of holes at an interface between the electron block layer and the emitting layer, slow down deterioration of a material of the electron block layer at the interface, and make an exciton composite region move toward a center of the emitting layer.

In an exemplary embodiment, an energy level collocation, a mobility collocation, or a collocation of an energy level and mobility among a hole transport layer, an electron block layer, a Host material of an emitting layer, a Dopant material of an emitting layer, and a hole block layer are beneficial to effective energy transfer, reduce an accumulation of carriers at an interface, improve stability of the interface and material, reduce material deterioration and life declination caused by electron accumulation, meanwhile, it is beneficial to transmit carriers to the emitting layer, increase a carrier density inside the emitting layer, improve a balance of carriers in the emitting layer, facilitate excitons to compositely emit light in the emitting layer, make an exciton composite region move to a center of the emitting layer, and improve efficiency and service life.

In an exemplary embodiment, $HOMO_{Host}$ may be about −5.70 eV to −6.10 eV, $HOMO_{Dopant}$ may be about −5.25 eV to −5.50 eV, $HOMO_{HBL}$ may be about −6.10 eV to −6.40 eV, $LUMO_{Host}$ may be about −2.70 eV to −3.10 eV, LUMO Dopant may be about −2.60 eV to −2.80 eV, and $LUMO_{HBL}$ may be about −2.55 eV to −2.80 eV.

In an exemplary embodiment, the hole mobility of the hole transport layer $EK_{HTL}$ may be about 104 cm²/Vs to $10^{-5}$ cm²/Vs, and the hole mobility of the electron block layer $EK_{EBL}$ may be about $10^{-5}$ cm²/Vs to $10^{-7}$ cm²/Vs.

In an exemplary embodiment, the electron mobility of the hole block layer $E_{HBL}$ may be about $10^{-5}$ cm²/Vs to $10^{-8}$ cm²/Vs, and the electron mobility of the Host material of the emitting layer $E_{Host}$ may be about $10^{-6}$ cm²s to $10^{-8}$ cm²/Vs.

In an exemplary embodiment, $HOMO_{Host}$ may be about −5.75 eV to −6.05 eV, $HOMO_{Dopant}$ may be about −5.3 eV to −5.45 eV, $HOMO_{HBL}$ may be about −6.15 eV to −6.35 eV, $LUMO_{Host}$ may be about −2.75 eV to −3.05 eV, $LUMO_{Dopant}$ may be about −2.65 eV to −2.75 eV, and $LUMO_{HBL}$ may be about −2.60 eV to −2.75 eV.

In an exemplary embodiment, a HOMO energy level and a LUMO energy level may be measured by photoelectron spectrophotometer (AC3/AC2) or ultraviolet (UV) spectroscopy, mobility may be measured by Space Charge Limited Current method (SCLC), and triplet energy level (Ti) may be measured by low temperature phosphorescence spectrometer (T1=1240/PL peak).

In an exemplary embodiment, a thickness of an emitting layer 50 is about 10 nm to 60 nm.

In an exemplary embodiment, a thickness of a hole block layer 60 is about 0.1 nm to 20 nm.

In an exemplary embodiment, a thickness of an electron block layer 40 is about 5 nm to 70 nm.

In an exemplary embodiment, a thickness of a hole transport layer 30 is about 80 nm to 120 nm.

In an exemplary embodiment, a thickness of the emitting layer 50 is different from that of the hole block layer 60. For example, a thickness of the emitting layer 50 may be greater than that of the hole block layer 60.

In an exemplary embodiment, a thickness of the emitting layer 50 is different from that of the electron block layer 40. For example, a thickness of the emitting layer 50 may be greater than that of the electron block layer 40.

In an exemplary embodiment, a thickness of the emitting layer 50 may be about 15 nm to 30 nm, a thickness of the hole block layer 60 may be about 5 nm to 15 nm, and a thickness of the electron block layer 40 may be about 5 nm to 15 nm.

In an exemplary embodiment, the emitting layer includes a host material and a dopant material doped in the host material, and a doping ratio of the dopant material of the emitting layer is 1% to 20%. Within a range of the doping ratio, on the one hand, the host material of the emitting layer may effectively transfer exciton energy to the dopant material of the emitting layer to excite the dopant material of the emitting layer to emit light, on the other hand, the host material of the emitting layer dilutes the dopant material of the emitting layer, which effectively improves fluorescence quenching caused by a collision between molecules of the dopant material of the emitting layer and a collision between energies, and improves a luminance efficiency and device life.

In an exemplary embodiment of the present disclosure, a doping ratio refers to a ratio of mass of the dopant material to mass of the emitting layer, that is, mass percentage. In an exemplary embodiment, the host material and the dopant material are co-evaporated through a multi-source evaporation process, so that the host material and the dopant material are uniformly dispersed in the emitting layer. A doping ratio may be adjusted by controlling an evaporation rate of the dopant material or by controlling an evaporation rate ratio of the host material to the dopant material during an evaporation process.

In an exemplary embodiment, the emitting layer is a blue emitting layer. An overall performance of an organic light emitting device may be better improved by increasing a luminance efficiency and service life of the blue emitting layer.

In an OLED structure, an exciton composite region is mainly concentrated at an interface between the emitting layer and the electron block layer, which makes excessive electrons accumulate at the interface. The accumulated electrons will lead to a material cracking of the electron block layer, thus reducing stability and a lifespan of the material. According to an exemplary embodiment of the present disclosure, by setting an energy level relationship and an electron mobility relationship among a host material of the emitting layer, a dopant material of the emitting layer, and a material of the hole block layer, a probability of electrons moving towards the hole block layer in the host material of the emitting layer may be increased, and an accumulation of electrons at an interface between the emitting layer and the electron block layer may be effectively reduced, which not only improves material stability of the electron block layer, reduces material deterioration and performance degradation caused by the electron accumulation, and prolongs a service life, but also effectively combines electrons in the emitting layer into excitons to emit light, and makes an exciton composite region move towards a center of the emitting layer, thereby improving a luminance efficiency.

In an exemplary embodiment, a host material of the emitting layer may include anthracene derivatives (including tritium substituted compounds), 9,10-(2-naphthyl)anthracene (AND) or 2-methyl-9,10-(2-naphthyl)anthracene (MAND), etc., which has features of high fluorescence quantum yield, easy modification and high thermal stability of molecular structures. Electron mobility of the host material of the emitting layer, $E_{Host}$ may be about $10^{-6}$ cm$^2$/Vs to $10^{-8}$ cm$^2$/Vs.

In an exemplary embodiment, a host material of the emitting layer may include, but is not limited to, compounds having structures shown in Formula 1-1 to Formula 1-3.

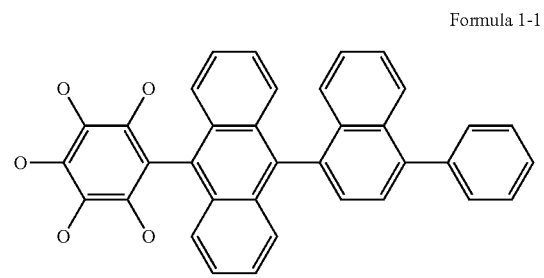

Formula 1-1

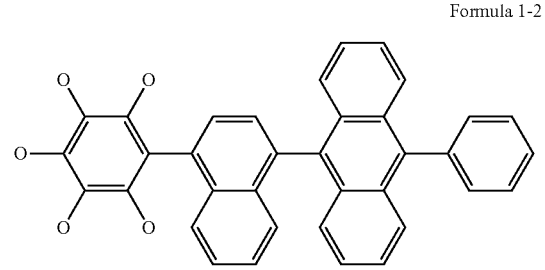

Formula 1-2

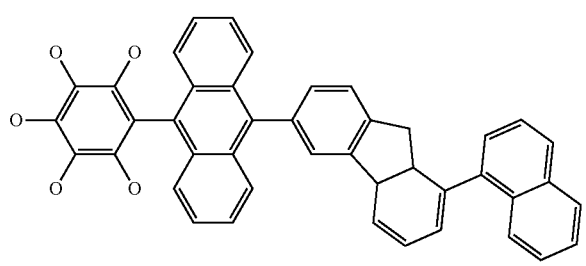

Formula 1-3

D is tritium.

In an exemplary embodiment, a dopant material of the emitting layer may include, but is not limited to, a compound having a structure shown in Formula 2.

Formula 2

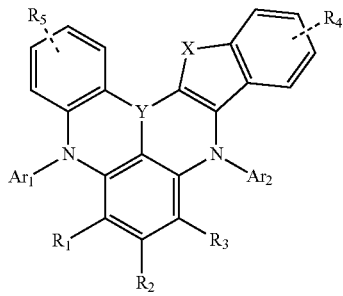

X is oxygen (O) or sulfur (S); Y is N-R7, B (boron), P (phosphorus); R1 to R3 are hydrogen, deuterium, fluorine, C1-C4 alkyl, C3-C10 cycloalkyl, C1-C30 alkylsilyl, or C6-C10 arylsilyl; R4 and R5 are hydrogen, deuterium, fluorine, C1-C4 alkyl, C3-C10 cycloalkyl, C1-C30 alkylsilyl, or C6-C30 arylsilyl, substituted or unsubstituted C6-C30 aryl or heteroaryl; $Ar_1$ and $Ar_2$ are substituted or unsubstituted C6-C30 aryl or heteroaryl; and R1 to R3 may be the same, or may be different.

The compound of the structure shown in Formula 2 is fused through a Core, and Y and N (nitrogen) are connected to aryl or heteroaryl, so that torsion of a single bond is inhibited, a molecular rigidity is increased, a material rigidity is increased, and nonradiative migration is reduced; moreover, structures of ground state and excited state change little, and a Stokes shift is relatively small. Since the structures of ground state and excited state change little, lifespan and color purity (narrowed spectrum) are improved, and a rigid planar skeleton is beneficial to quantum yield and efficiency improvement. By introducing deuterium and silyl groups, heat resistance and decomposition resistance of materials may be improved.

In an exemplary embodiment, a dopant material of the emitting layer may include, but is not limited to, compounds having structures shown in Formula 2-1 to Formula 2-9.

Formula 2-1

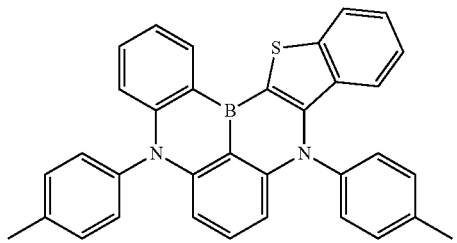

Formula 2-2

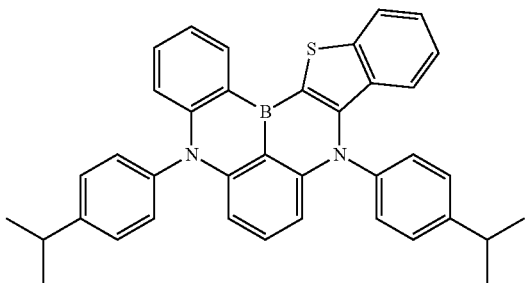

Formula 2-3

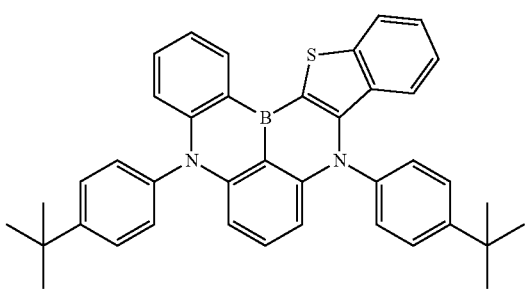

Formula 2-4

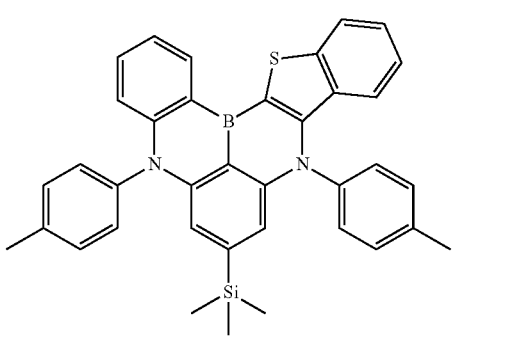

Formula 2-5

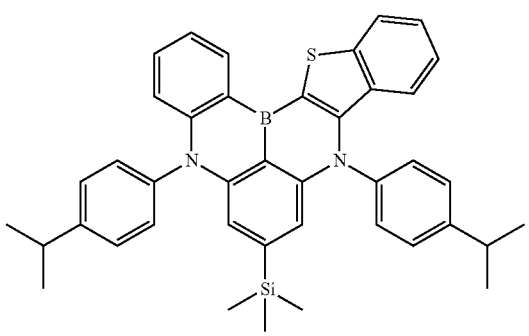

Formula 2-6

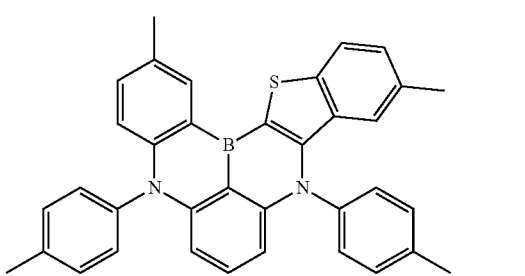

-continued

Formula 2-7

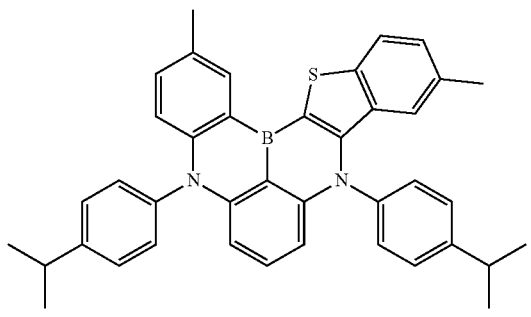

Formula 2-8

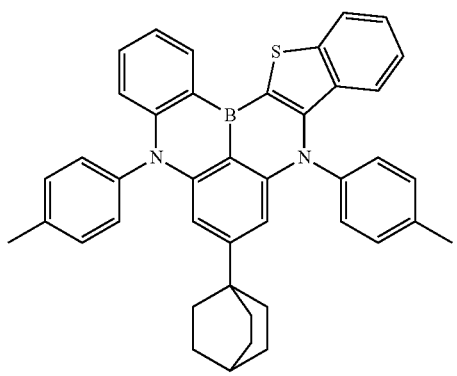

Formula 2-9

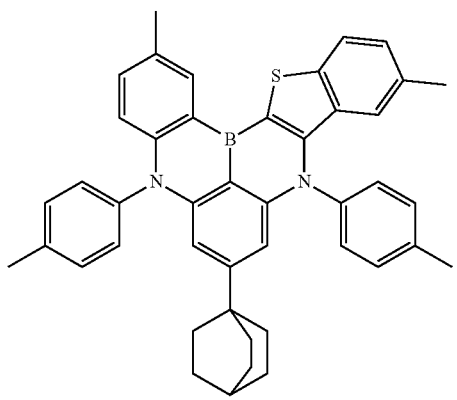

In an exemplary embodiment, a material of the hole block layer includes, but is not limited to, a compound having a structure of Formula 3-1.

Formula 3-1

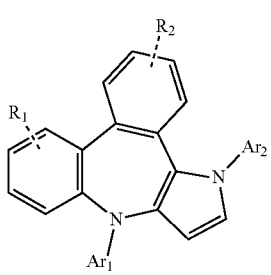

R1 and R2 are hydrogen, deuterium, and fluorine, C1-C4 alkyl, C3-C10 cycloalkyl, C1-C30 alkylsilyl or C6-C10 arylsilyl; $Ar_1$ and $Ar_2$ are substituted or unsubstituted C6-C30 aryl or heteroaryl, one of which is heteroaryl containing at least one nitrogen; R1 and R2 may be the same or different; $Ar_1$ and $Ar_2$ are different.

In an exemplary embodiment, a material of the hole block layer includes, but is not limited to, a compound having a structure of Formula 3-2.

Formula 3-2

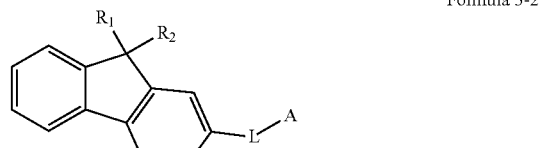

L is substituted or unsubstituted C6-C30 aryl or heteroaryl; A is a substituted or unsubstituted nitrogen-containing aromatic heterocyclic, which contains at least one nitrogen atom; R1 and R2 are methyl or aryl; R1 and R2 may be the same or different.

In an exemplary embodiment, a material of the hole block layer includes, but is not limited to, compounds having structures of Formula 3-3 to Formula 3-14.

Formula 3-3

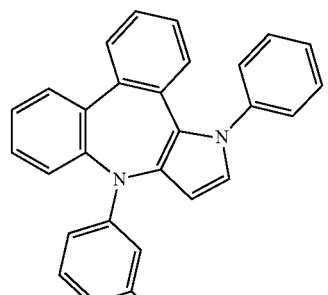
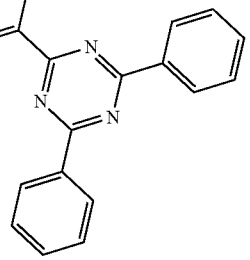

Formula 3-4
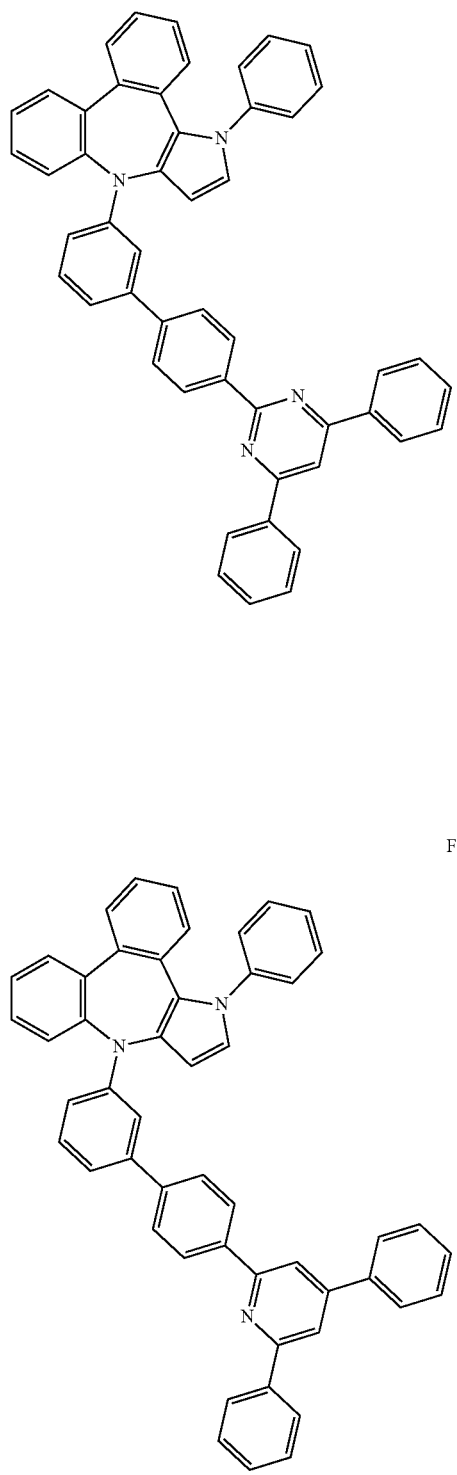
Formula 3-5
Formula 3-6
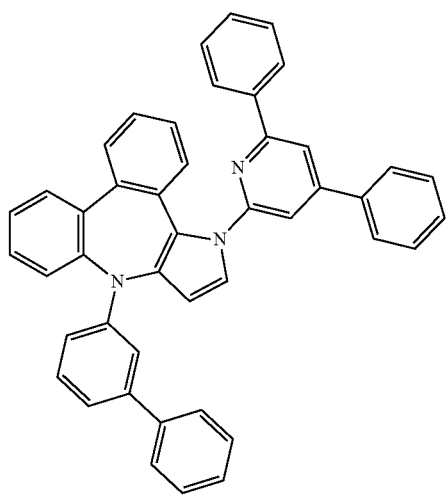
Formula 3-7
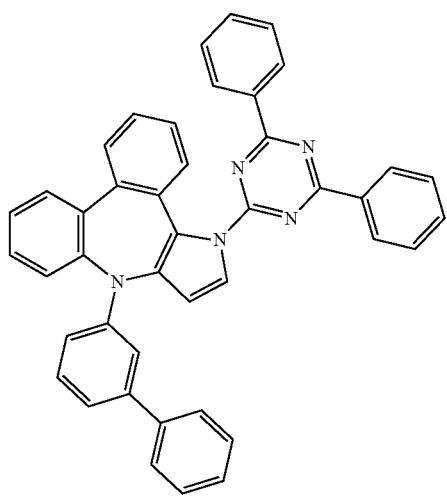
Formula 3-8
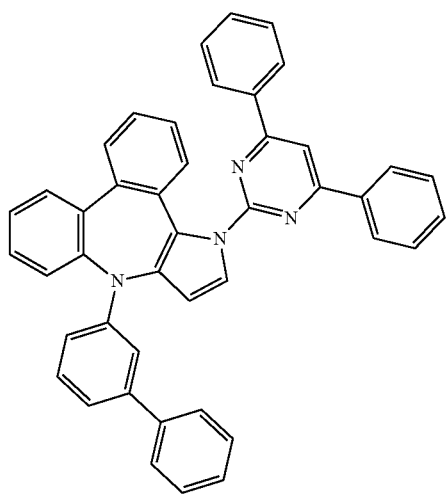

Formula 3-9
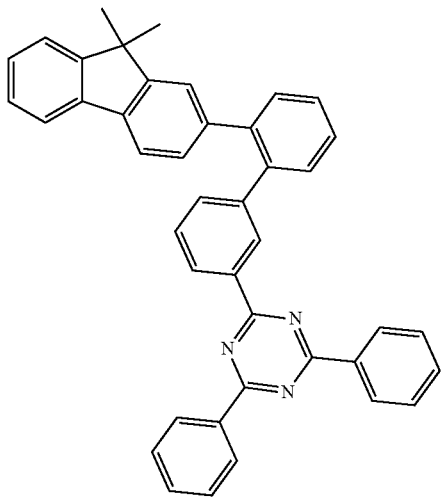
Formula 3-10
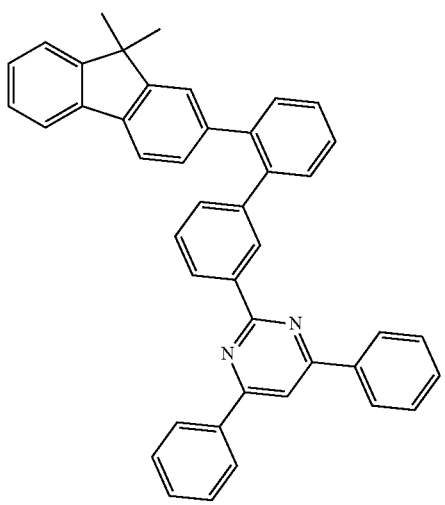
Formula 3-11
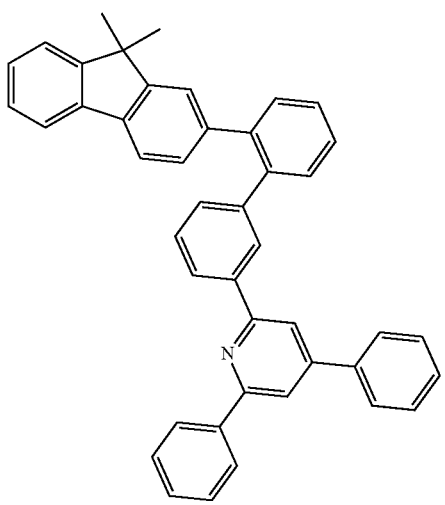
Formula 3-12
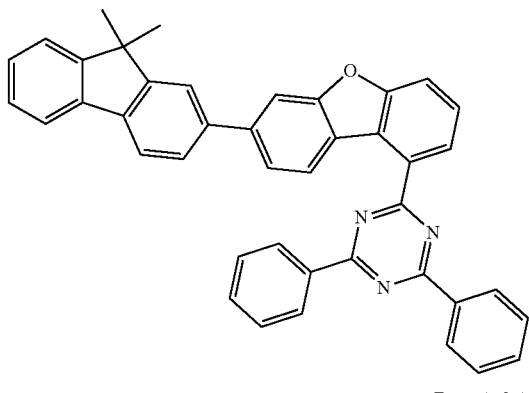
Formula 3-13
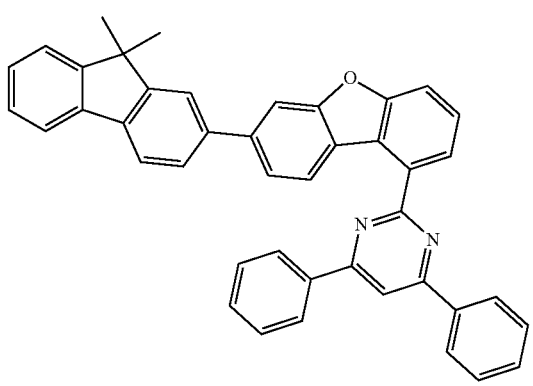
Formula 3-14
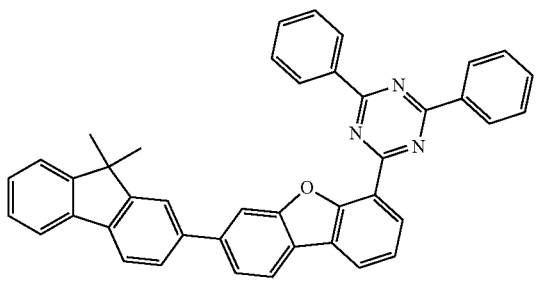
In an exemplary embodiment, a material of the electron block layer includes, but is not limited to, compounds having structures of Formula 4-1 or Formula 4-2.
Formula 4-1
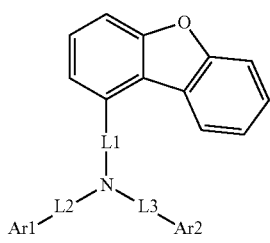

Formula 4-2

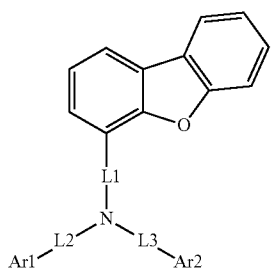

L1-L3 are single bond and C6-C15 aryl; $Ar_1$, $Ar_2$ are substituted or unsubstituted C6-C40 aryl, arylamino, or fluorenyl, $Ar_1$ and $Ar_2$ are different groups one of which may be a substituent represented by Formula 5.

Formula 5

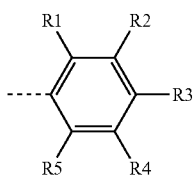

R1-R5 are hydrogen, deuterium, alkyl, cycloalkyl, or C6-C36 aryl.

In an exemplary embodiment, in Formula 4-1 and Formula 4-2, one of Ar and $Ar_2$ may be a substituent represented by Formula 5-1 to Formula 5-7.

Formula 5-1

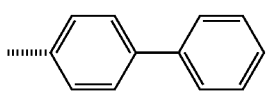

Formula 5-2

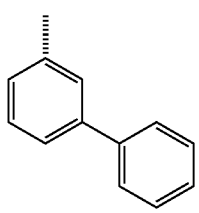

Formula 5-3

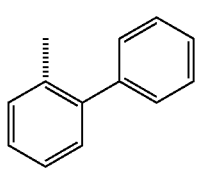

Formula 5-4

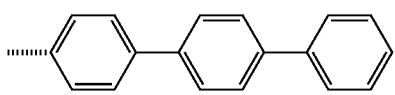

Formula 5-5

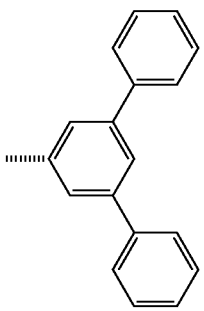

Formula 5-6

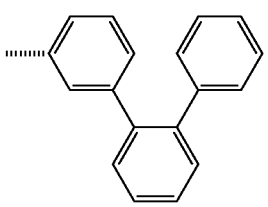

Formula 5-7

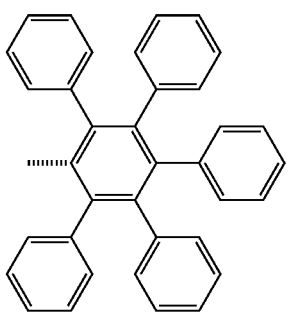

Compounds with structures shown in Formula 4-1 and Formula 4-2 are asymmetric structures, which may improve thermal stability of materials, inhibit crystallization, and improve stability of thin films. In an exemplary embodiment, hole mobility of the electron block layer may be about $10^{-5}$ cm²/Vs to $10^{-7}$ cm²/Vs.

In an exemplary embodiment, a material of the electron block layer includes, but is not limited to, compounds having structures of Formula 4-1-1 to Formula 4-1-6.

Formula 4-1-1

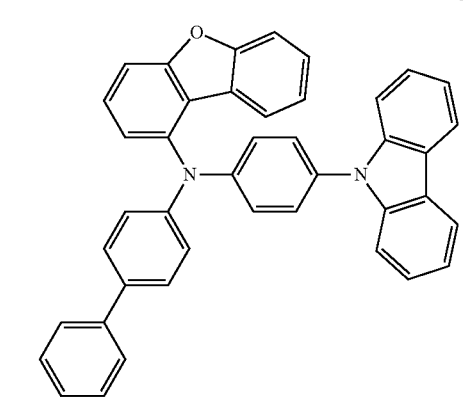

Formula 4-1-2
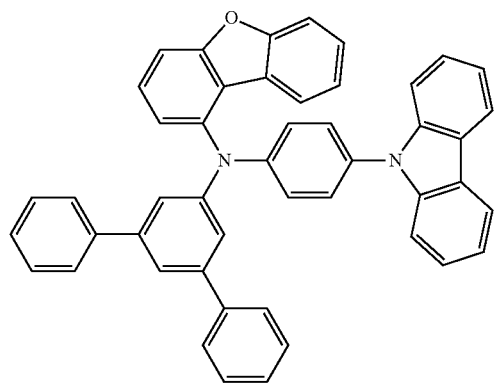
Formula 4-1-3
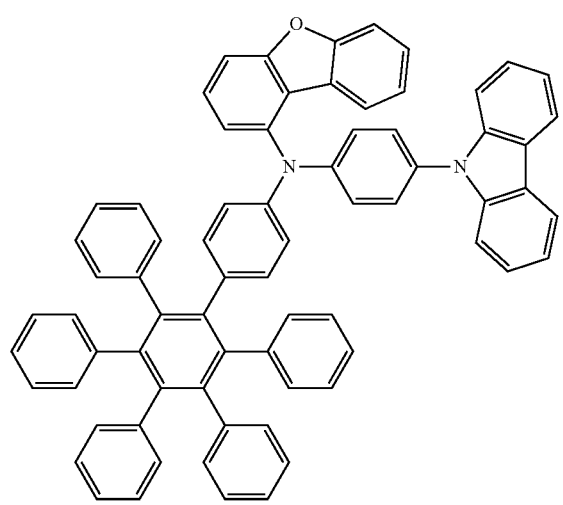
Formula 4-1-4
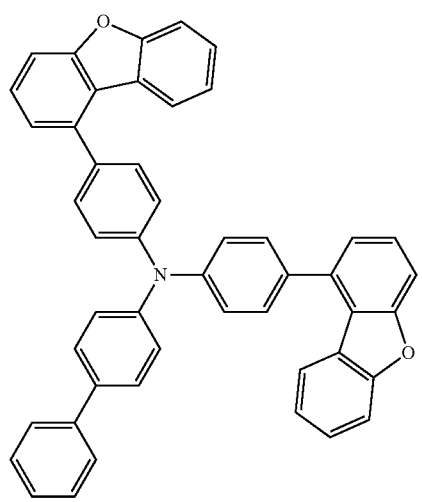
Formula 4-1-5
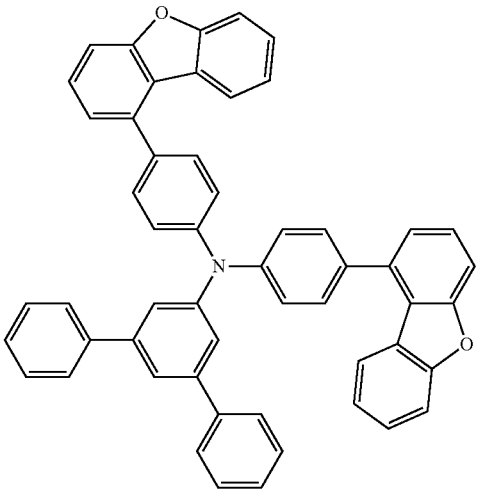
Formula 4-1-6
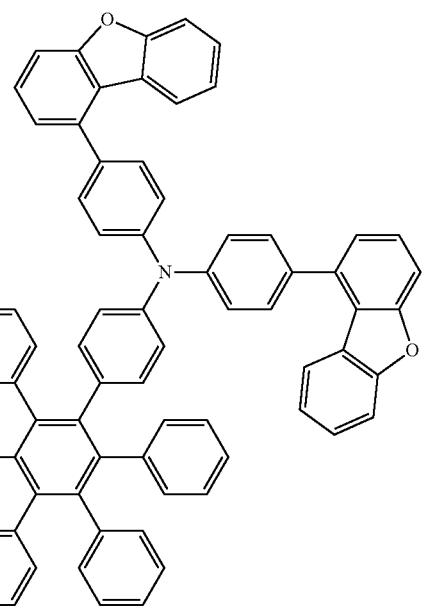
In an exemplary embodiment, a material of the electron block layer includes, but is not limited to, compounds having structures of Formula 4-2-1 to Formula 4-2-6.
Formula 4-2-1

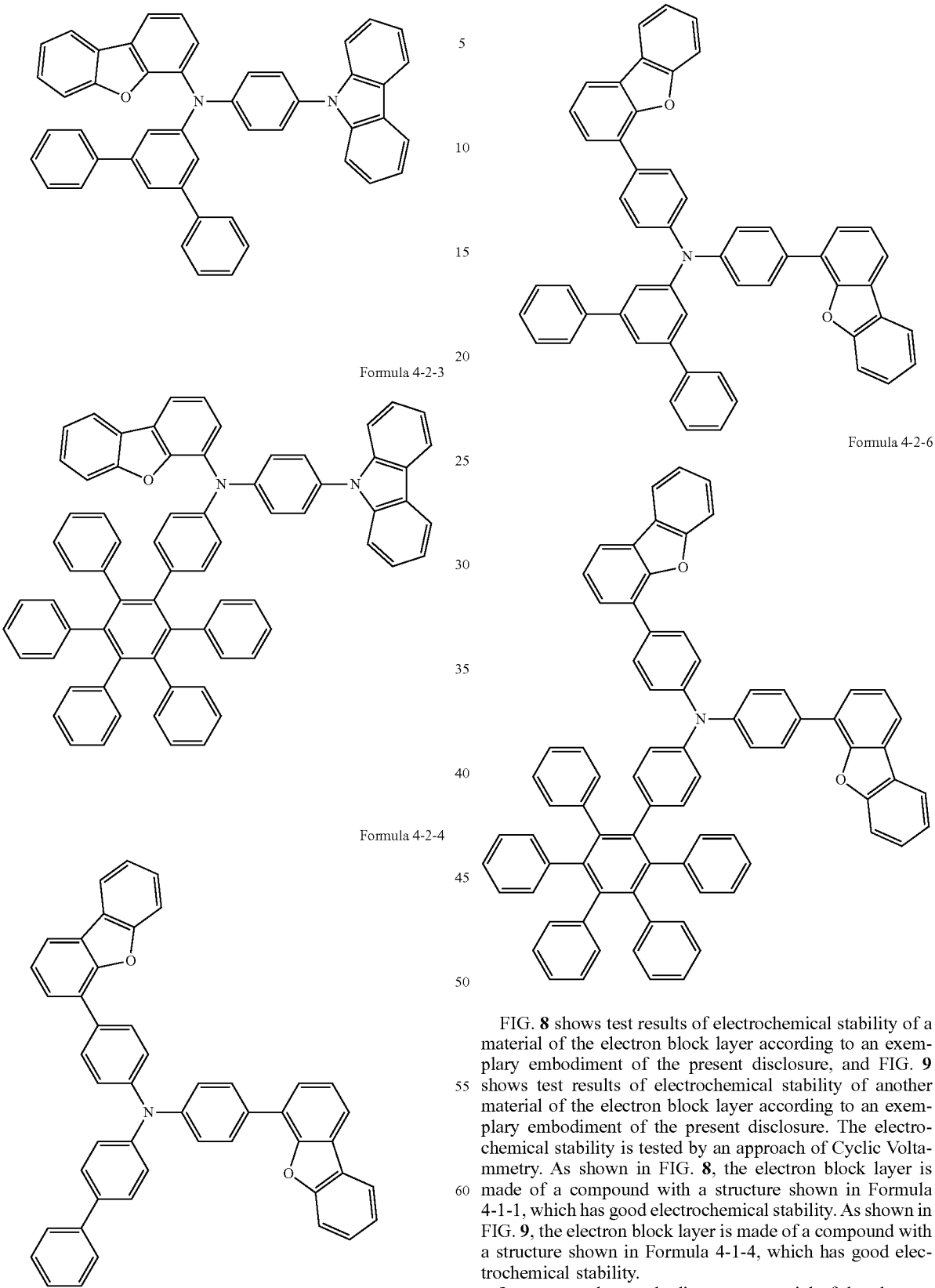

Figure 8:
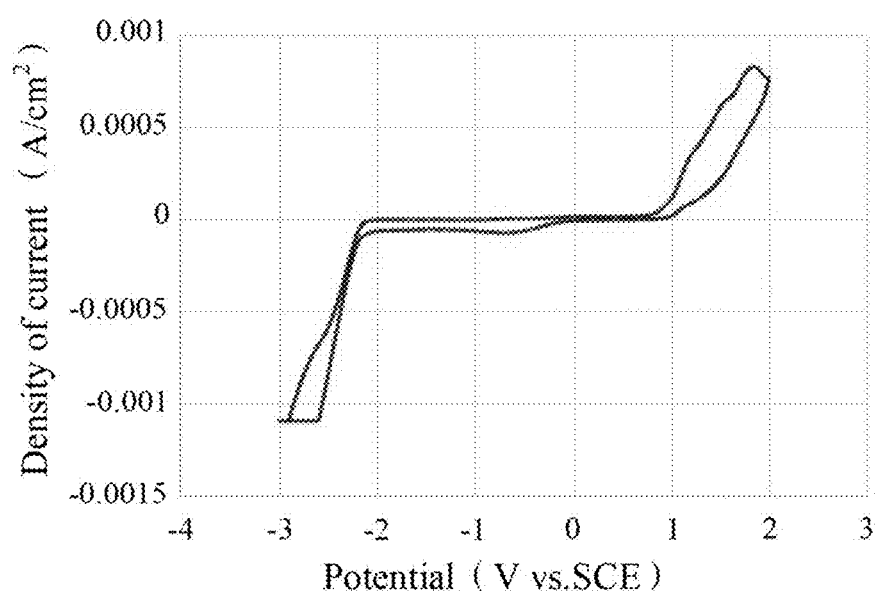
FIG. 8 is test results of electrochemical stability of an electron block layer according to an exemplary embodiment of the present disclosure.
Figure 9:
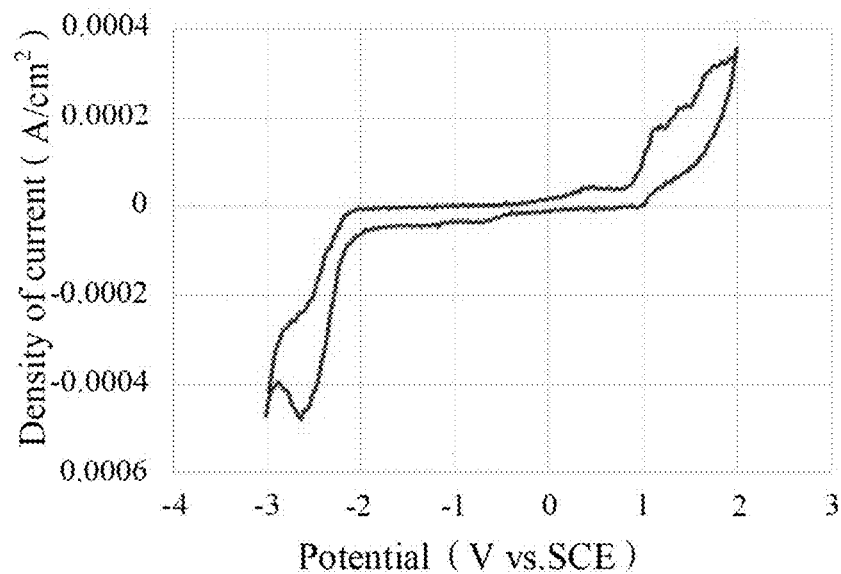
FIG. 9 is test results of electrochemical stability of another electron block layer according to an exemplary embodiment of the present disclosure.

FIG. 8 shows test results of electrochemical stability of a material of the electron block layer according to an exemplary embodiment of the present disclosure, and FIG. 9 shows test results of electrochemical stability of another material of the electron block layer according to an exemplary embodiment of the present disclosure. The electrochemical stability is tested by an approach of Cyclic Voltammetry. As shown in FIG. 8, the electron block layer is made of a compound with a structure shown in Formula 4-1-1, which has good electrochemical stability. As shown in FIG. 9, the electron block layer is made of a compound with a structure shown in Formula 4-1-4, which has good electrochemical stability.

In an exemplary embodiment, a material of the electron block layer, a host material of the emitting layer, a dopant material of the emitting layer, and a material of the hole block layer may be other materials known by those skilled in the art that satisfy the above-mentioned energy level relationship and mobility relationship, which is not limited hereto in the present disclosure.

Figure 10:
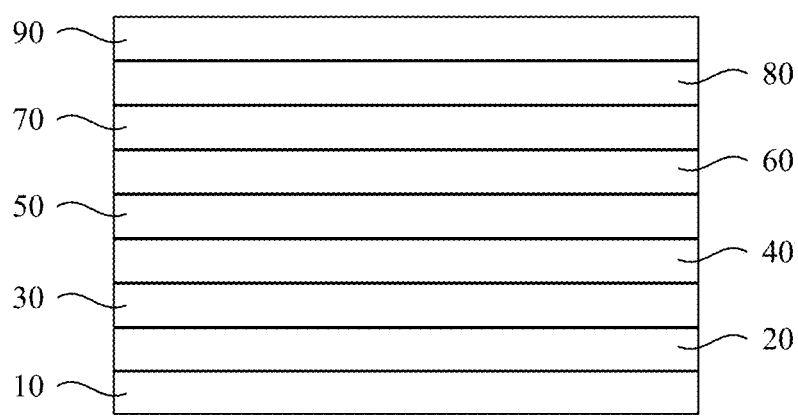
FIG. 10 is a schematic diagram of another OLED structure according to an exemplary embodiment of the present disclosure.

FIG. 10 is a schematic diagram of another OLED structure according to an exemplary embodiment of the present disclosure. As shown in FIG. 10, the OLED includes an anode 10, a cathode 90, and an organic emitting layer disposed between the anode 10 and the cathode 90. In an exemplary embodiment, the organic emitting layer may include a hole injection layer 20, a hole transport layer 30, an electron block layer 40, an emitting layer 50, a hole block layer 60, an electron transport layer 70, and an electron injection layer 80 which are stacked. The hole injection layer 20, the hole transport layer 30 and the electron block layer 40 are disposed between the anode 10 and the emitting layer 50; the hole injection layer 20 is connected to the anode 10, and the electron block layer 40 is connected to the emitting layer 50; the hole transport layer 30 is disposed between the hole injection layer 20 and the electron block layer 40. The hole block layer 60, the electron transport layer 70 and the electron injection layer 80 are disposed between the emitting layer 50 and the cathode 90; the hole block layer 60 is connected to the emitting layer 50; the electron injection layer 80 is connected to the cathode 90; and the electron transport layer 70 is disposed between the hole block layer 60 and the electron injection layer 80. In an exemplary embodiment, the hole injection layer 20 is configured to lower a barrier of injecting holes from the anode, so that the holes may be efficiently injected into the emitting layer 50 from the anode. The hole transport layer 30 is configured to realize directional and orderly controlled migration of injected holes. The electron block layer 40 is configured to form a migration barrier for electrons and prevent electrons from migrating out of the emitting layer 50. The emitting layer 50 is configured to combine electrons and holes to emit light. The hole block layer 60 is configured to form a migration barrier for holes and prevent holes from migrating out of the emitting layer 50. The electron transport layer 70 is configured to realize directional and orderly controlled migration of injected electrons. The electron injection layer 80 is configured to lower a barrier of injecting electrons from the cathode, so that the electrons may be efficiently injected into the emitting layer 50 from the cathode.

In an exemplary embodiment, structures and materials of the emitting layer 50 and the hole block layer 60 are the same as or similar to those of the previous embodiments, which will not be repeatedly described here.

In an exemplary embodiment, the anode may be made of a material having a high work function. For a bottom emission type, the anode may be made of a transparent oxide material, such as indium tin oxide (ITO) or indium zinc oxide (IZO), and a thickness of the anode may be about 80 nm to 200 nm. For a top emission type, the anode may be made of a composite structure of metal and transparent oxide, such as Ag/ITO, Ag/IZO, or ITO/Ag/ITO. A thickness of a metal layer in the anode may be about 80 nm to 100 nm, and a thickness of the transparent oxide in the anode may be about 5 nm to 20 nm, so that an average reflectivity of the anode in a visible light region is about 85%-95%.

In an exemplary embodiment, for an OLED of a top emission type, the cathode may be made of a metal material and be formed through an evaporation process. The metal material may be magnesium (Mg), silver (Ag), or aluminum (Al), or alloy material such as Mg:Ag alloy, with a ratio of Mg:Ag being about 9:1 to 1:9. A thickness of the cathode may be about 10 nm to 20 nm so that an average transmittance of the cathode at a wavelength of 530 nm is about 50%-60%. For an OLED of a bottom emission type, the cathode may be made of magnesium (Mg), silver (Ag), aluminum (Al), or Mg:Ag alloy. A thickness of the cathode may be greater than about 80 nm, so that the cathode has good reflectivity.

In an exemplary embodiment, the hole injection layer may be made of an inorganic oxide, such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide, or may be made of P-type dopants with strong electron-withdrawing systems and dopants of hole transport materials, such as hexacyanohexaazatriphenylene, 2,3,5,6-Tetrafluoro-7,7',8,8'-tetracyanoquinodimethane (F4-TCNQ) dimethyl or 1,2,3-tri[(cyano)(4-cyano-2,3,5,6-tetrafluorophenyl)methylene]cyclopropane.

In an exemplary embodiment, a thickness of the hole injection layer may be about 5 nm to 20 nm.

In an exemplary embodiment, the hole transport layer may be made of materials with high hole mobility, such as aromatic amines with hole transport features, and its substituent groups may be carbazole, methylfluorene, spirofluorene, dibenzothiophene, or furan, such as 4,4'-bis [N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluoren-9-yl)triphenylamine (BAFLP), 4,4'-bis[N-(9,9-dimethylfluoren-2-yl)-N-phenylamino]biphenyl (DFLDPBi), 4,4'-bis(9-carbazolyl)biphenyl (CBP) or 9-phenyl-3-[4-(10-phenyl-9-anthryl)phenyl]-9H-carbazole (PCzPA).

In an exemplary embodiment, a thickness of the hole transport layer may be about 80 nm to 120 nm, and a conductivity of the hole transport layer is less than or equal to a conductivity of the hole injection layer.

In an exemplary embodiment, the electron block layer may be made of aromatic amines with hole transport features, and its substituent groups may be carbazole, methylfluorene, spirofluorene, dibenzothiophene, or furan, such as 4,4'-bis[N-(1-naphthyl)-N-phenylamino]biphenyl (NPB), N,N'-bis(3-methylphenyl)-N,N'-diphenyl-[1,1'-biphenyl]-4, 4'-diamine (TPD), 4-phenyl-4'-(9-phenylfluoren-9-yl)triphenylamine (BAFLP), 4,4'-bis[N-(9,9-dimethylfluoren-2-yl)-N-phenylamino]biphenyl (DFLDPBi), 4,4'-bis(9-carbazolyl)biphenyl (CBP) or 9-phenyl-3-[4-(10-phenyl-9-anthryl)phenyl]-9H-carbazole (PCzPA).

In an exemplary embodiment, a thickness of the electron block layer may be about 5 nm to 70 nm. A conductivity of the electron block layer is less than or equal to that of the hole injection layer.

In an exemplary embodiment, the electron transport layer may use aromatic heterocyclic compounds, for example, imidazole derivatives such as benzimidazole derivatives, imidazopyridine derivatives, and benzimidazophenanthridine derivatives; azine derivatives such as pyrimidine derivatives and triazine derivatives; quinoline derivatives, isoquinoline derivatives, phenanthroline derivatives, compounds containing a nitrogen-containing six-membered ring structure (including compounds having a phosphine oxide-based substituent on the heterocyclic ring), etc. For example, 2-(4-biphenyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-tert-butylphenyl)-4-phenyl-5-(4-biphenyl)-1,2,4-Triazole (TAZ), 3-(4-tert-butylphenyl)-4-(4-ethylphenyl)-5-(4-biphenyl)-1,2,4-triazole (p-EtTAZ), bathophenanthroline (BPhen), bathocuproine (BCP), or 4,4'-bis(5-methylbenzoxazol-2-yl)stilbene (BzOs), etc.

In an exemplary embodiment, a thickness of the electron transport layer may be about 20 nm to 50 nm.

In an exemplary embodiment, the electron injection layer may use an alkali metal or a metal, such as lithium fluoride (LiF), ytterbium (Yb), magnesium (Mg), or Calcium (Ca), or compounds of these alkali metals or metals.

In an exemplary embodiment, a thickness of the electron injection layer may be about 0.5 nm to 5 nm.

In an exemplary embodiment, the OLED may include an encapsulation layer, which may be encapsulated by a cover plate, or be encapsulated by a thin film.

In an exemplary embodiment, for an OLED of a top emission type, a thickness of an organic emitting layer between the cathode and the anode may be designed to meet optical path requirements of an optical microresonator, so as to obtain an optimal intensity and a color of an emitted light.

In an exemplary embodiment, the following preparation method may be used to prepare a display substrate including an OLED structure. First, a drive circuit layer is formed on a substrate through a patterning process, and a drive circuit layer of each sub-pixel may include a drive transistor and a storage capacitor constituting a pixel drive circuit. Then, a planarization layer is formed on the substrate on which the aforementioned structure is formed, and a via hole exposing a drain electrode of the drive transistor is formed on a planarization layer of each sub-pixel. An anode is formed through a patterning process on the substrate on which the aforementioned structure is formed, and an anode of each sub-pixel is connected to the drain electrode of the drive transistor through the via hole on the planarization layer. Subsequently, a pixel define layer is formed through a patterning process on the substrate on which the aforementioned structure is formed, a pixel opening exposing the anode is formed on the pixel define layer of each sub-pixel, and each pixel opening serves as an emitting region of each sub-pixel. On the substrate on which the aforementioned structure is formed, an open mask is used to evaporate a hole injection layer and a hole transport layer in sequence to form a common layer of the hole injection layer and the hole transport layer on the display substrate. That is, hole injection layers of all sub-pixels are connected and hole transport layers of all sub-pixels are connected. A thickness of the hole injection layer may be about 5 nm to 20 nm, and a thickness of the hole transport layer may be about 80 nm to 120 nm. For example, areas of the hole injection layer and the hole transport layer are approximately the same, but thicknesses are different. Subsequently, a fine metal mask is used to evaporate the electron block layer and a red emitting layer, the electron block layer and a green emitting layer, and the electron block layer and a blue emitting layer in different sub-pixels, and electron block layers and emitting layers of adjacent sub-pixels may overlap in a small portion (for example, an overlap portion accounts for less than 10% of an area of a pattern of a respective emitting layer), or may be isolated. A thickness of the electron block layer may be about 5 nm to 70 nm, and a thickness of the emitting layer may be about 10 nm to 60 nm. Then, an open mask is used to evaporate the hole block layer, the electron transport layer, the electron injection layer and the cathode in sequence to form a common layer of the hole block layer, the electron transport layer, the electron injection layer and the cathode on the display substrate. That is, hole block layers of all sub-pixels are connected, electron transport layers of all sub-pixels are connected, electron injection layers of all sub-pixels are connected, and cathodes of all sub-pixels are connected. A thickness of the hole block layer may be about 0.1 nm to 20 nm, and a thickness of the electron transport layer may be about 20 nm to 50 nm.

In an exemplary embodiment, the blue emitting layer includes a blue light host material (BH) and a blue light dopant material (BD), and a doping ratio may be about 1% to 20%. A multi-source co-evaporation method may be adopted to evaporate the blue emitting layer to form an emitting layer containing a host material and a dopant material. A doping ratio may be adjusted by controlling an evaporation rate of the dopant material or by controlling an evaporation rate ratio of the host material to the dopant material during an evaporation process.

In an exemplary embodiment, orthographic projections of one or more of the hole injection layer, the hole transport layer, the hole block layer, the electron transport layer, the electron injection layer, and the cathode on the base substrate is continuous. In some examples, at least one layer of the hole injection layer, the hole transport layer, the hole block layer, the electron transport layer, the electron injection layer, and the cathode of at least one row or column of sub-pixels is connected. In some examples, at least one layer of the hole injection layer, the hole transport layer, the hole block layer, the electron transport layer, the electron injection layer, and the cathode of a plurality of sub-pixels is connected.

In an exemplary embodiment, the organic emitting layer may include a microcavity adjusting layer located between the hole transport layer and the emitting layer. For example, after the hole transport layer is formed, a fine metal mask is used to respectively evaporate a red microcavity adjusting layer and the red emitting layer, a green microcavity adjusting layer and the green emitting layer, and a blue microcavity adjusting layer and the blue emitting layer in different sub-pixels. In an exemplary embodiment, the red microcavity adjusting layer, the green microcavity adjusting layer, and the blue microcavity adjusting layer may include an electron block layer.

In an exemplary embodiment, since the hole block layer is a common layer and an emitting layers of different sub-pixels are isolated, an orthographic projection of the hole block layer on the substrate includes an orthographic projection of the emitting layer on the substrate, and an area of the hole block layer is larger than that of the emitting layer.

In an exemplary embodiment, since the hole block layer is a common layer, an orthographic projection of the hole block layer on the substrate includes at least orthographic projections of emitting regions of two sub-pixels on the substrate.

In an exemplary embodiment, an orthographic projection of emitting layers of at least part of sub-pixels on the substrate overlaps an orthographic projection of a pixel drive circuit on the substrate.

Table 1 is performance comparison results of several film material combination structures according to an exemplary embodiment of the present disclosure. In a comparative experiment, structures of organic emitting layers of comparative structure 1 and a structure 1 to a structure 6 are all HIL/HTL/EBL/BEML/HBL/ETL, and thicknesses of corresponding film layers of the comparative structure 1 and the structure 1 to the structure 6 are the same. Materials and thicknesses of hole injection layers (HILs), hole transport layers (HTLs), electron block layers (EBLs), and electron transport layers (ETLs) of the comparative structure 1 and the structure 1 to the structure 6 are the same; and blue light host materials of the comparative structure 1 and the structure I to the structure 6 are the same.

Related materials of film layers with the same material in the comparative structure 1 and the structure 1 to the structure 6 are as follows.

| Project | Material |
|---|---|
| Hole Injection Layer (HIL) | 2,3,5,6-tetrafluoro-7,7′,8,8′-tetracyandimethyl-p-benzoquinone (F4TCNQ) 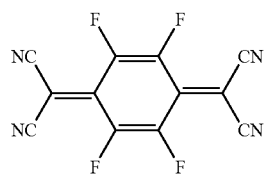 |
| Hole Transport Layer (HTL) | 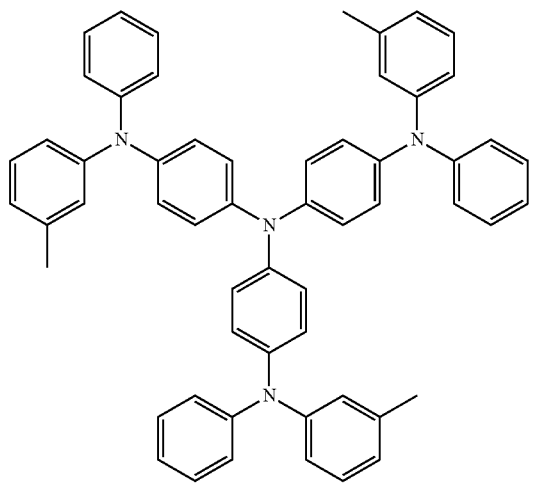 [SMILES: Cc1cccc(N(c2ccccc2)c2ccc(N(c3ccc(N(c4ccccc4)c4cccc(C)c4)cc3)c3ccc(N(c4ccccc4)c4cccc(C)c4)cc3)cc2)c1] |
| Electron Block Layer (EBL) | 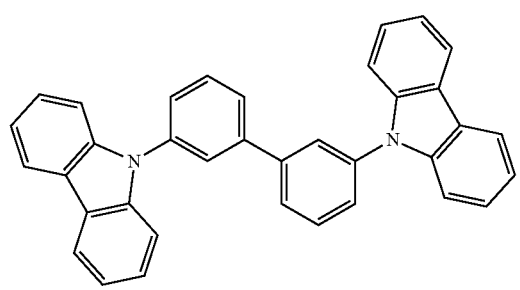 [SMILES: c1cc(-c2cccc(-n3c4ccccc4c4ccccc43)c2)cc(-n2c3ccccc3c3ccccc32)c1] |
| Electron Transport Layer (ETL) | 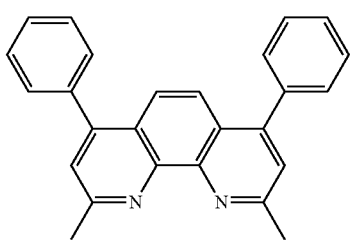 [SMILES: Cc1cc(-c2ccccc2)c2ccc3c(-c4ccccc4)cc(C)nc3c2n1] |

| Project | Material |
|---|---|
| Blue Light Host Material | 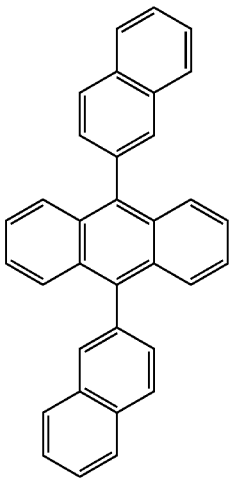 [SMILES: c1ccc2cc(-c3c4ccccc4c(-c4ccc5ccccc5c4)c4ccccc34)ccc2c1] |

In the comparative experiment, blue light emitting layers (BEMLs) of the comparative structure 1 and the structure 1 to the structure 6 all include a blue light host material and a blue light dopant material with a doping ratio of 3%. Blue light dopant materials of the comparative structure 1 and the structure 1 to structure 6 are different, and materials of hole block layers (HBLs) of the comparative structure 1 and the structure 1 to the structure 6 are different. The blue light dopant materials and materials of the hole block layers (HBLs) of the comparative structure 1 and the structure 1 to the structure 6 are as follows.

| | Blue Light Dopant Material | Material of Hole Block Layer (HBL) |
|---|---|---|
| Comparative Structure | 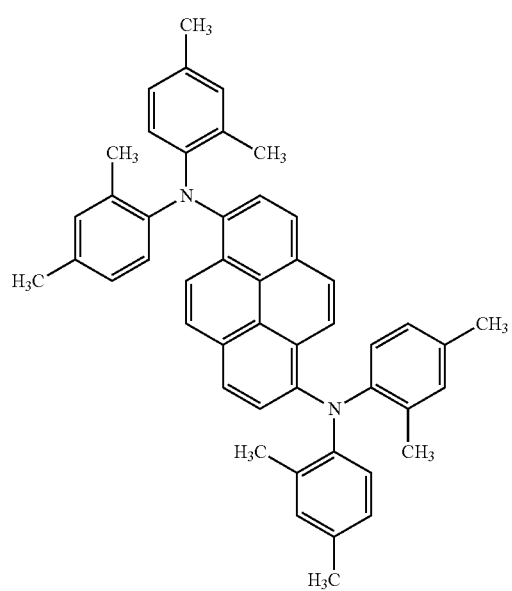 | 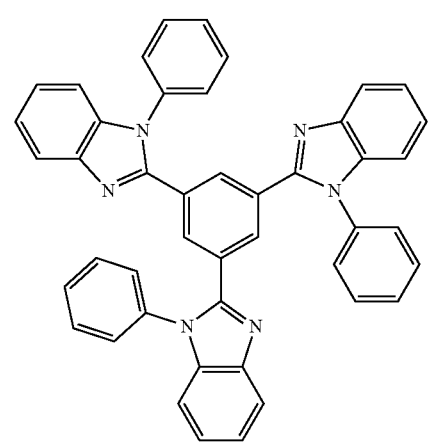 [SMILES: c1ccc(-n2c(-c3cc(-c4nc5ccccc5n4-c4ccccc4)cc(-c4nc5ccccc5n4-c4ccccc4)c3)nc3ccccc32)cc1] |

-continued
| Blue Light Dopant Material | Material of Hole Block Layer (HBL) |
|---|---|
| Structure 1    Formula 2-4 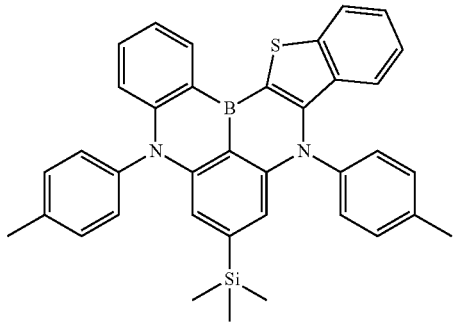 | Formula 3-3 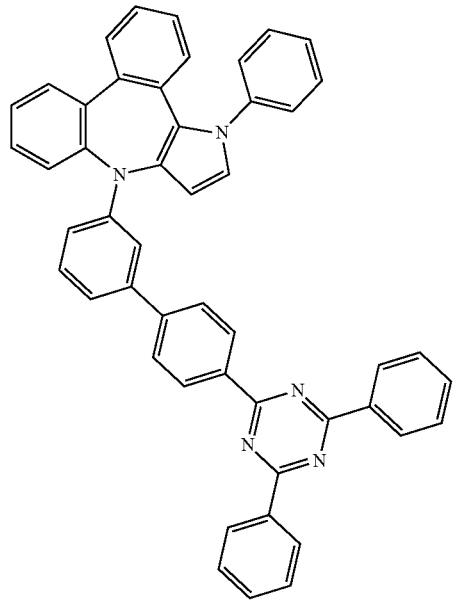 |
| Structure 2    Formula 2-4 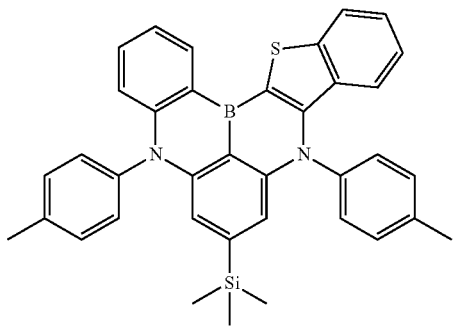 | Formula 3-9 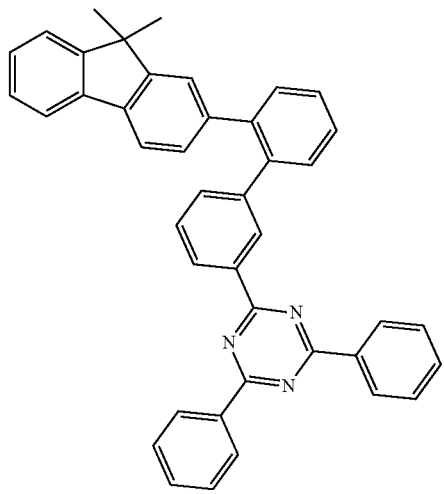 |

-continued
| Blue Light Dopant Material | Material of Hole Block Layer (HBL) |
|---|---|
| Structure 3  Formula 2-4 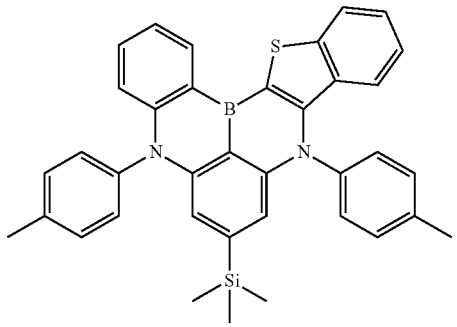 | Formula 3-7 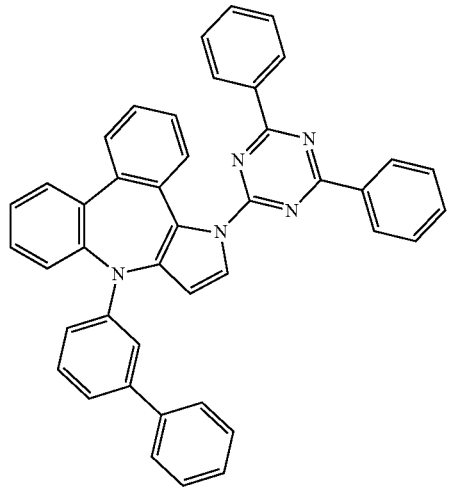 |
| Structure 4  Formula 2-4 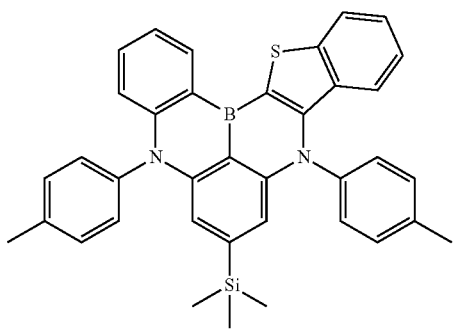 | Formula 3-12 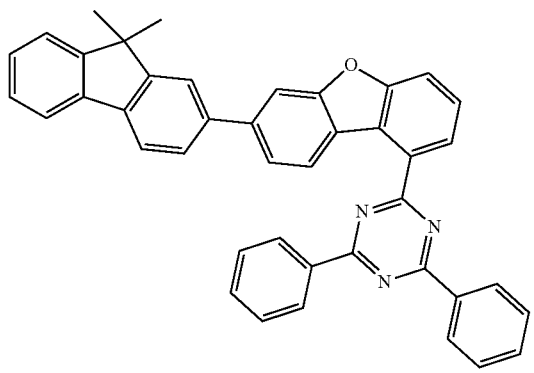 |
| Structure 5  Formula 2-9 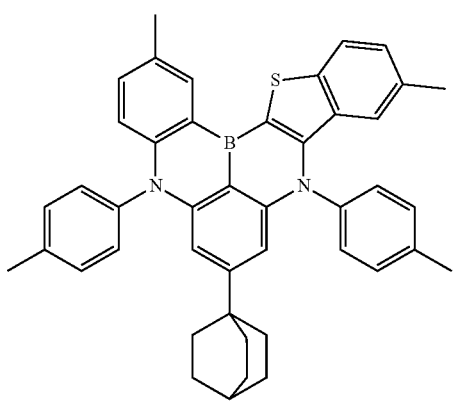 | Formula 3-3 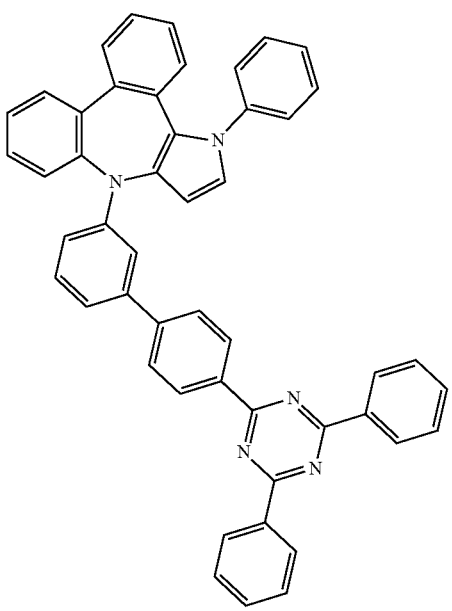 |

-continued

| Blue Light Dopant Material | Material of Hole Block Layer (HBL) |
|---|---|
| Structure 6  Formula 2-9 | Formula 3-9 |

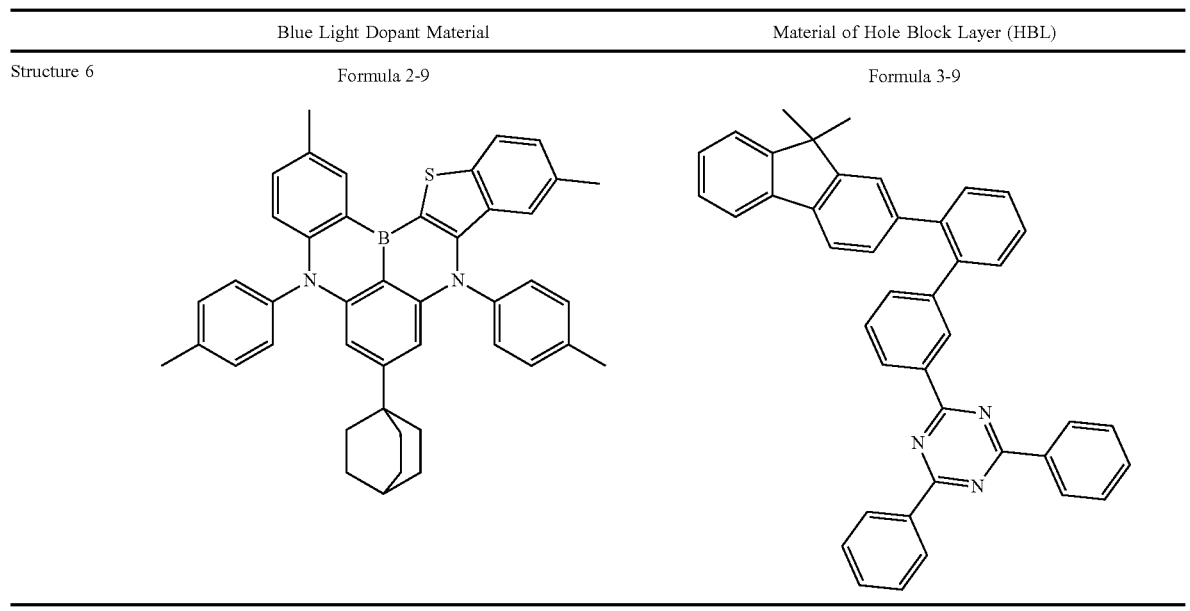

TABLE 1

Performance comparison results of several different dopant materials of emitting layers and materials of hole block layers

|  | Voltage | Efficiency | Lifespan |
|---|---|---|---|
| Comparative Structure 1 | 100% | 100% | 100% |
| Structure 1 | 96% | 120% | 118% |
| Structure 2 | 94% | 131% | 126% |
| Structure 3 | 98% | 118% | 109% |
| Structure 4 | 93% | 113% | 128% |
| Structure 5 | 95% | 118% | 104% |
| Structure 6 | 97% | 122% | 121% |

Figure 11:
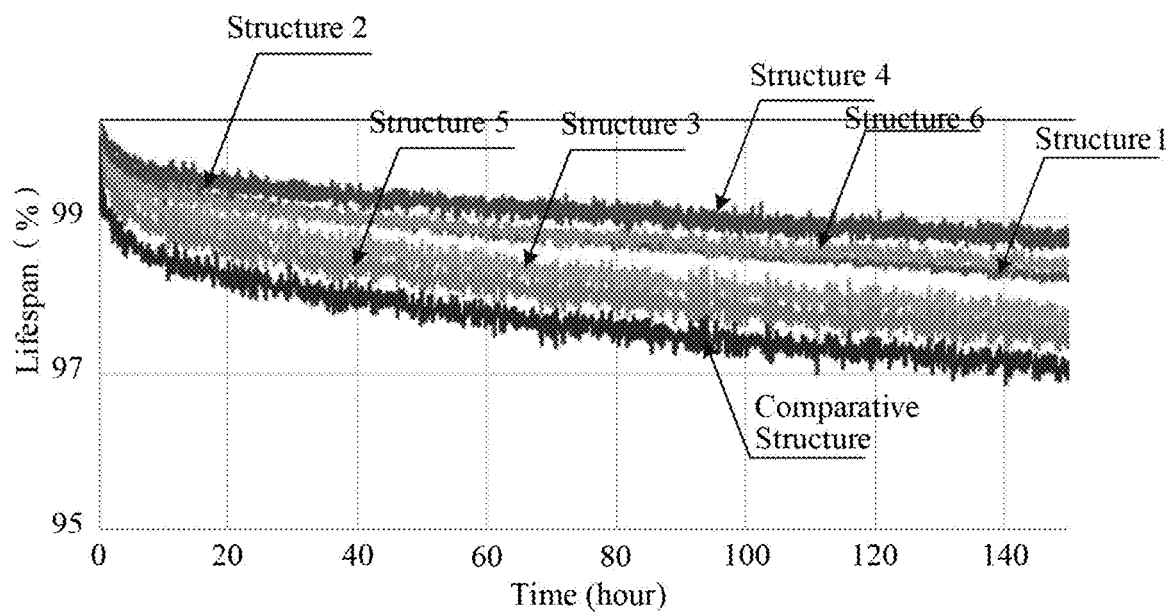
FIG. 11 is a schematic diagram of life spans of combination structures of several different dopant materials and materials of hole block layers.

FIG. 11 is a schematic diagram of lifespans of several different combinations of dopant materials and materials of hole block layers. As shown in Table 1 and FIG. 11, compared with the comparative structure 1, the structure 1 to the structure 6 have a significant progress in voltage reduction, efficiency improvement, and lifespan extension. At the same time, a reduction in lifespans of the structure 1 to the structure 6 is smaller than that of the comparative structure 1. Blue light dopant materials of the structure 2 and the structure 4 contain trimethyl silicon substitution, and thermal stability of the materials is high, so an increase in lifespans of the structure 2 and the structure 4 is greater than an increase in a lifespan of the structure 5. Materials of hole block layers of the structure 2 and the structure 4 are relatively long lifespan materials. Although a blue light dopant material of the structure 3 contains trimethyl silicon substitution, since materials of hole block layers are different, an increase in a lifespan of the structure 3 is less than the increase in the lifespans of the structure 2 and the structure 4. Mobility of materials of hole block layers of the structure 2 and structure 6 is larger, so an increase in efficiencies of structures 2 and 6 is greater than that of other structures. Energy level collocations of a host material, a dopant material, and a material of a hole block layer in structure 2 is more reasonable, thus an increase in an efficiency is greater. According to an exemplary embodiment of the present disclosure, by reasonably collocating an energy level relationship and a mobility relationship among a host material of an emitting layer, a dopant material of the emitting layer and a material of a hole block layer, a probability of electrons in the host material of the emitting layer moving towards the hole block layer may be increased, and an accumulation of electrons at an interface between the emitting layer and the electron block layer may be effectively reduced, which not only improves material stability of the electron block layer, reduces material deterioration and performance degradation caused by the electron accumulation, and prolongs a service life, but also effectively combines hole-electron pairs in the emitting layer to emit light, and makes an exciton composite region move towards a center of the emitting layer, thereby improving a luminance efficiency. According to the exemplary embodiment of the present disclosure, by optimizing a dopant material and a material of the hole block layer, crystallinity and stability of materials are effectively improved, a life attenuation caused by material deterioration is avoided, and a lifespan of a device is maximally prolonged.

Figure 12:
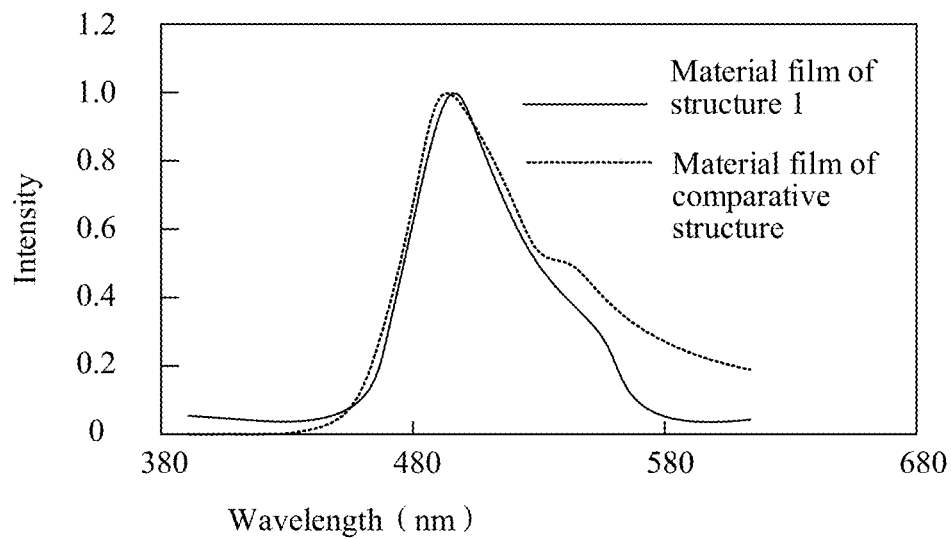
FIG. 12 is a spectrogram of different dopant material films.

FIG. 12 is a spectrogram of different dopant material films. A material film of the structure 1 formed by evaporation of the blue light dopant material of the structure 1 is represented by solid lines, and a material film of the comparative structure formed by evaporation of the blue light dopant material of the comparative structure 1 is represented by dotted lines, and a fluorescence spectrum is tested through a fluorescence spectrometer. As shown in FIG. 12, the blue light dopant material proposed in the present disclosure has a narrower emission spectrum compared with the blue light dopant material of the comparative structure, which is beneficial to an improvement of color purity.

Table 2 is performance comparison results of another several film layer material combination structures according to an exemplary embodiment of the present disclosure. In a comparative experiment, structures of organic emitting layers of comparative structure 2 and a structure 7 to a structure 10 are all HIL/HTL/EBL/BEML/HBL/ETL, and thicknesses of corresponding film layers of the comparative structure 2 and the structure 7 to the structure 10 are the same. Materials and thicknesses of hole injection layers (HILs), hole transport layers (HTLs), hole block layers (HBLs), and electron transport layers (ETLs) of the comparative structure 1 and the structure 1 to the structure 10 are the same; and blue light dopant materials of the comparative structure 2 and the structure 7 to the structure 10 are the same.

Related materials of film layers with the same material in the comparative structure 2 and Project Material

| Project | Material |
| --- | --- |
| Hole Injection Layer (HIL) | 2,3,5,6-tetrafluoro-7,7',8,8'-tetracyandimethyl-p-benzoquinone (F4TCNQ) |
| Hole Transport Layer (HTL) | |
| Hole Block Layer (HBL) | |
| Electron Transport Layer (ETL) | |

| Project | Material |
|---|---|
| Blue Light Host Material | 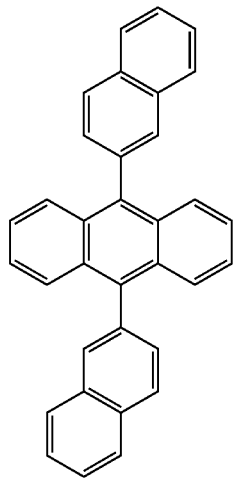 [SMILES: c1ccc2cc(-c3c4ccccc4c(-c4ccc5ccccc5c4)c4ccccc34)ccc2c1] |

In the comparative experiment, blue emitting layers (BEMLs) of the comparative structure 2 and the structure 7 to the structure 10 all include a blue light host material and a blue light dopant material with a doping ratio of 5%. Materials of electron block layers (EBLs) of the comparative structure 2 and the structure 7 to the structure 10 are different, and blue light dopant materials are different. The materials of the electron block layers (EBLs) and the blue light dopant materials of the comparative structure 2 and the structure 7 to the structure 10 are as follows.

| | Material of Electron Block Layer (EBL) | Blue Light Dopant Material |
|---|---|---|
| Comparative Structure 2 | 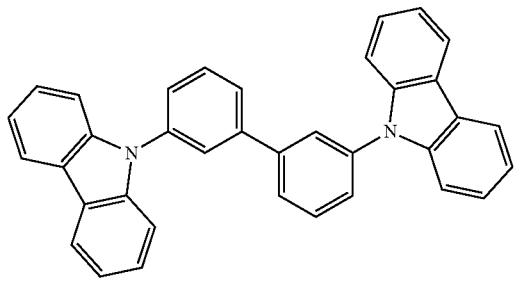 [SMILES: c1cc(-c2cccc(-n3c4ccccc4c4ccccc43)c2)cc(-n2c3ccccc3c3ccccc32)c1] | 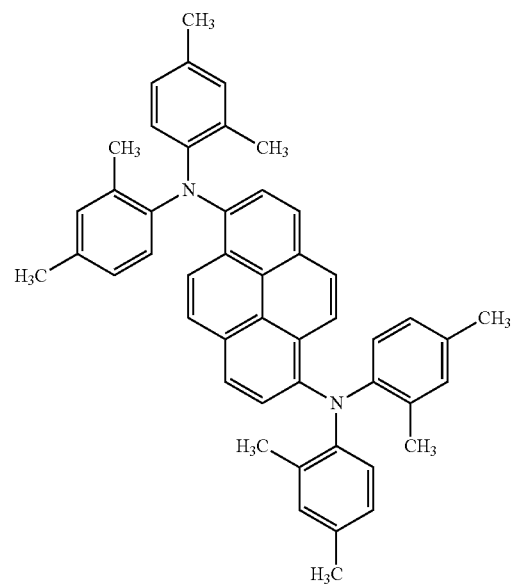 |

-continued
| | Material of Electron Block Layer (EBL) | Blue Light Dopant Material |
|---|---|---|
| Structure 7 | Formula 4-1-1 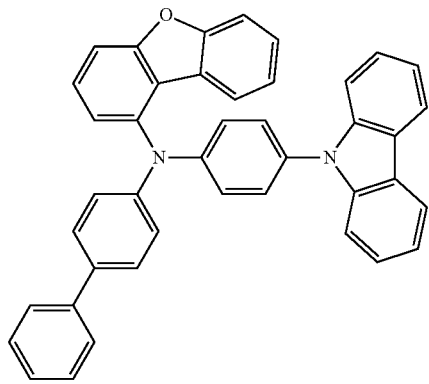 | Formula 2-4 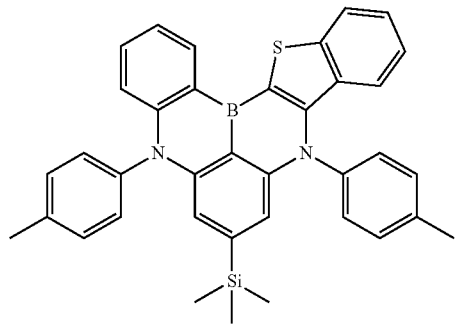 |
| Structure 8 | Formula 4-1-4 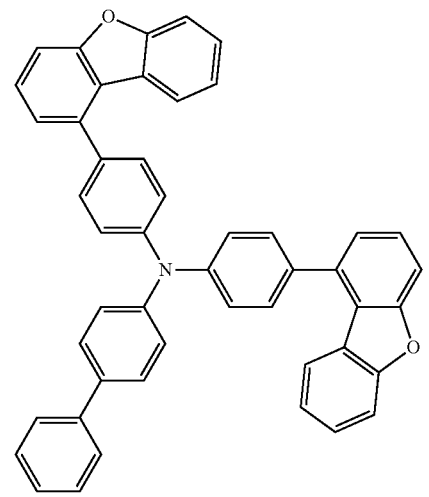 | Formula 2-4 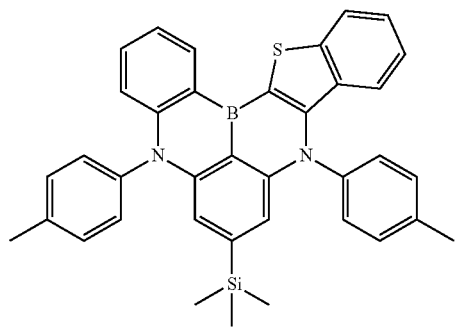 |
| Structure 9 | Formula 4-2-1 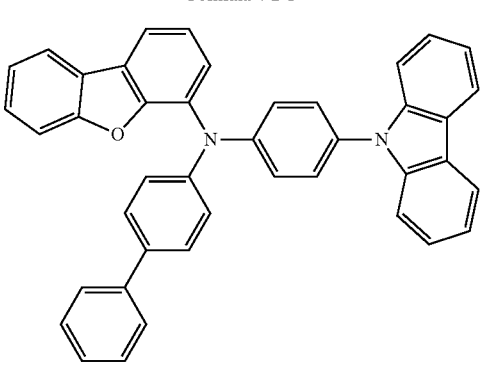 | Formula 2-4 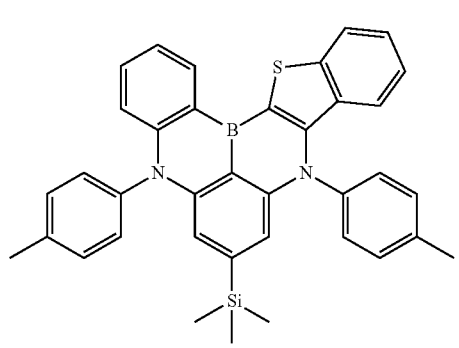 |

| Material of Electron Block Layer (EBL) | Blue Light Dopant Material |
|---|---|
| Structure 10 — Formula 4-2-4 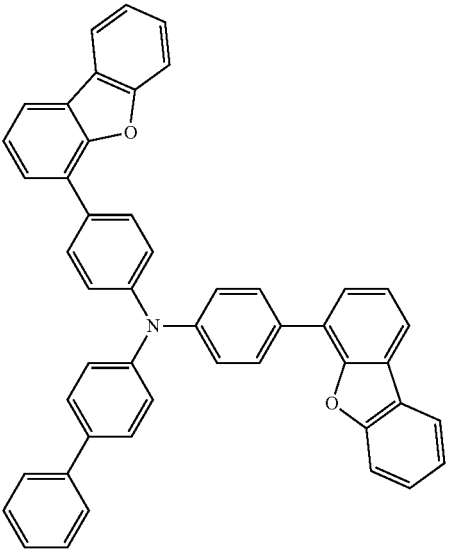 | Formula 2-4 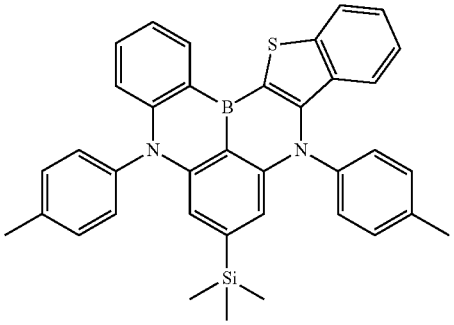 |

TABLE 2

Performance comparison results of several different electron block layers and emitting layer dopant materials

| | Voltage | Efficiency | Lifespan |
|---|---|---|---|
| Comparative Structure 2 | 100% | 100% | 100% |
| Structure 7 | 96% | 115% | 118% |
| Structure 8 | 95% | 118% | 121% |
| Structure 9 | 94% | 130% | 132% |
| Structure 10 | 93% | 124% | 122% |

As shown in Table 2, compared with the comparative structure 2, the structure 7 to structure 10 have a significant progress in voltage reduction, efficiency improvement, and lifespan extension, and through combinations of different electron block layers and emitting layer dopant materials, lifespans may be greatly improved.

In an exemplary embodiment, a reasonable collocation of an energy level relationship and a mobility relationship of an electron block layer and an emitting layer dopant material are beneficial to an effective energy transfer, a reduction in an accumulation of carriers at an interface, stability improvement of the interface and material, a reduction in material deterioration and life declination caused by electron accumulation, meanwhile, it is beneficial to transmit carriers to the emitting layer, increase a carrier density inside the emitting layer, improve a balance of carriers in the emitting layer, facilitate excitons to compositely emit light in the emitting layer, and make an exciton composite region move to a center of the emitting layer to improve efficiency and service life. According to an exemplary embodiment of the present disclosure, crystallinity and stability of materials are effectively improved by optimizing electron block layerls and dopant materials of the emitting layer and combining the electron block layers and the dopant materials of the emitting layer with high efficiency and good stability, thus avoiding a life attenuation caused by material deterioration and maximally prolonging a lifespan of a blue light emitting device.

The present disclosure further provides a display apparatus including the aforementioned organic light emitting device. The display apparatus may be any product or component with a display function such as a mobile phone, a tablet computer, a television, a display, a laptop, a digital photo frame, a navigator, a vehicle-mounted display, a smart watch, a smart band.

Although the embodiments disclosed in the present disclosure are as described above, the described contents are only the embodiments for facilitating understanding of the present disclosure, which are not intended to limit the present disclosure. Any person skilled in the field to which the present disclosure pertains may make any modifications and variations in the forms and details of implementation without departing from the spirit and the scope disclosed in the present disclosure, but the patent protection scope of the present application should still be subject to the scope defined by the appended claims.

What is claimed is:

1. An organic light emitting device, comprising an anode, a cathode, and an emitting layer disposed between the anode and the cathode, wherein the emitting layer comprises a host material and a dopant material doped in the host material; the host material and the dopant material satify:

$|HOMO_{Dopant}| < |HOMO_{Host}|, |LUMO_{Dopant}| \le |LUMO_{Host}|$;

where $HOMO_{Dopant}$ is a highest occupied molecular orbit (HOMO) energy level of the dopant material, $HOMO_{Host}$ is a HOMO energy level of the host material, $LUMO_{Dopant}$ is a lowest unoccupied molecular orbital (LUMO) energy level of the dopant material, and $LUMO_{Host}$ is a LUMO energy level of the host material:

wherein a hole block layer is further disposed between the emitting layer and the cathode, and wherein and the host material and the hole block layer satisfy:

|HOMO$_{HBL}$−HOMO$_{Host}$|≥0.5eV, and

E$_{HBL}$≥E$_{Host}$ wherein HOMO$_{HBL}$ is a HOMO energy level of the hole block layer, E$_{HBL}$ is an electron mobility of the hole block layer, and E$_{Host}$ is an electron mobility of the host material, and wherein electron mobility is measured by Space Charge Limited Current (SCLC) method.

2. The organic light emitting device of claim 1, wherein the dopant material and the hole block layer satisfy:

|HOMO$_{HBL}$−HOMO$_{Dopant}$|≥0.9eV.

3. The organic light emitting device of claim 1, wherein the host material and the hole block layer satisfy:

|LUMO$_{Host}$|>|LUMO$_{HBL}$| where LUMO$_{HBL}$ is a LUMO energy level of the hole block layer.

4. The organic light emitting device of claim 1, wherein the dopant material and a material of the hole block layer satisfy:

T1$_{HBL}$>T1$_{Dopant}$, where T1$_{HBL}$ is a lowest triplet energy of the hole block layer, and T1$_{Dopant}$ is a lowest triplet energy of the dopant material.

5. The organic light emitting device of claim 1, wherein a hole transport layer and an electron block layer are further disposed between the anode and the emitting layer, and the hole transport layer and the electron block layer satisfy:

|HOMO$_{HTL}$−HOMO$_{EBL}$|<0.3eV, where HOMO$_{HTL}$ is a HOMO energy level of the hole transport layer, and HOMO$_{EBL}$ is a HOMO energy level of the electron block layer.

6. The organic light emitting device of claim 5, wherein the electron block layer and the host material satisfy:

0.2eV≤HOMO$_{EBL}$−HOMO$_{Host}$|<0.5eV.

7. The organic light emitting device of claim 5, wherein the hole transport layer and the electron block layer satisfy:

EK$_{HTL}$>EK$_{EBL}$, where EK$_{HTL}$ is a hole mobility of the hole transport layer, and EK$_{EBL}$ is a hole mobility of the electron block layer.

8. The organic light emitting device of claim 1, wherein the host material comprises anthracene derivatives.

9. The organic light emitting device of claim 1, wherein the host material comprises one or more of the following compounds having the following structural formulas:

where D is deuterium.

10. The organic light emitting device of claim 1, wherein the dopant material comprises a compound having the following structural formula:

where X is oxygen (O) or sulfur (S); Y is B, P; R1 to R3 are hydrogen, deuterium, fluorine, C1-C4 alkyl, C3-C10 cycloalkyl, C1-C30 alkylsilyl, or C6-C10 arylsilyl; R4 and R5 are hydrogen, deuterium, fluorine, C1-C4 alkyl, C3-C10 cycloalkyl, C1-C30 alkylsilyl, or C6-C30 arylsilyl, C6-C30 aryl or heteroaryl; Ar$_1$ and Ar$_2$ are C6-C30 aryl or heteroaryl; and R1 to R3 are the same or different.

11. The organic light emitting device of claim 1, wherein the dopant material comprises one or more of the following compounds having the following structural formulas:

65
-continued

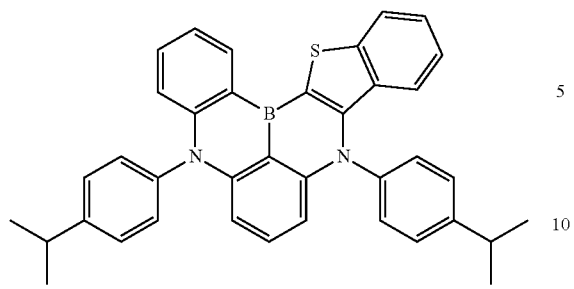

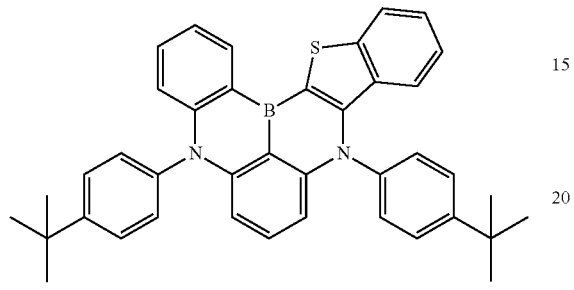

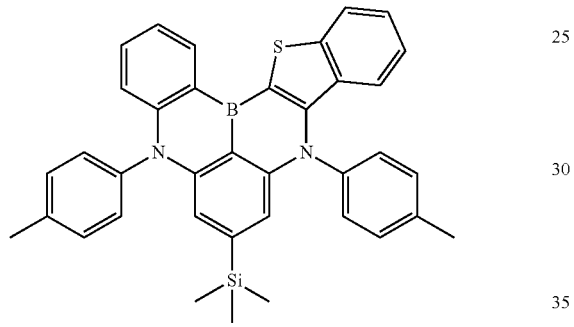

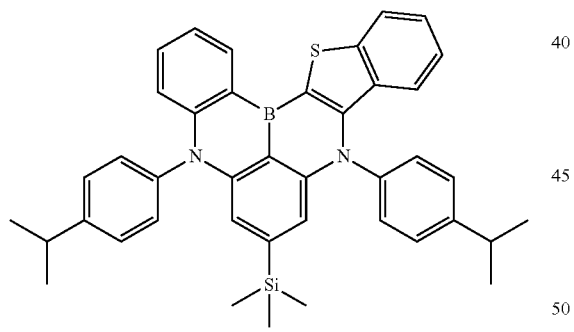

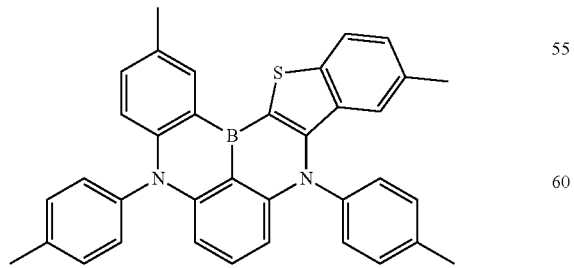

66
-continued

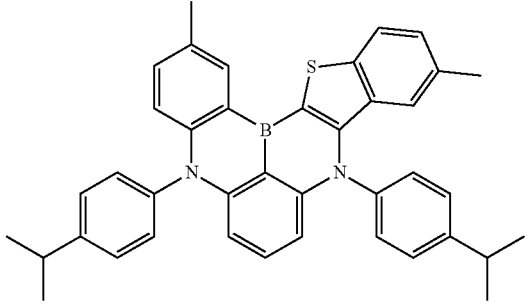

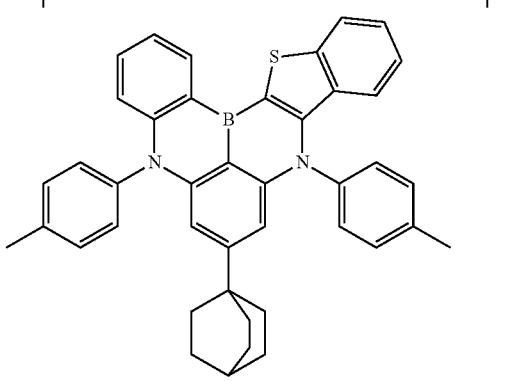

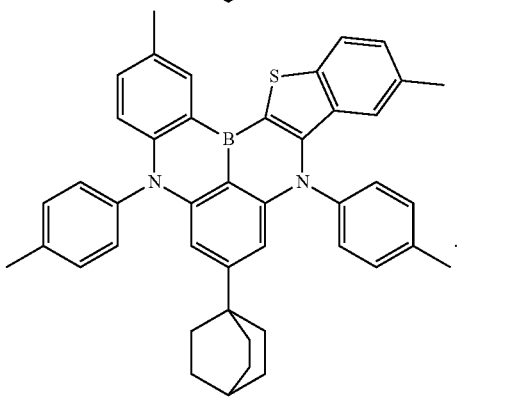

12. The organic light emitting device of claim 1, wherein the hole block layer comprises, but is not limited to, a compound having a structure represented by the following formula:

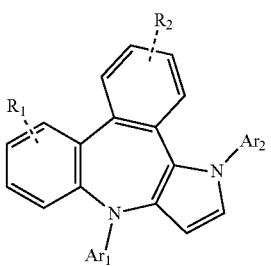

where R1 and R2 are hydrogen, deuterium, fluorine, C1-C4 alkyl, C3-C10 cycloalkyl, C1-C30 alkylsilyl, or C6-C10 arylsilyl; $Ar_1$ and $Ar_2$ are C6-C30 aryl or heteroaryl, one of which is heteroaryl containing at least one nitrogen; R1 and R2 are the same or different; and $Ar_1$ and $Ar_2$ are different;

or the hole block layer comprises, but is not limited to, a compound having a structure represented by the following formula:

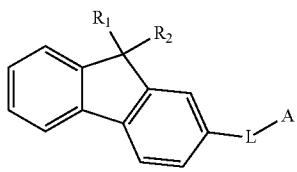

where L is C6-C30 aryl or heteroaryl; A is a nitrogen-containing aromatic heterocyclic which contains at least one nitrogen atom; R1 and R2 are methyl or aryl; R1 and R2 are the same or different;

or the hole block layer comprises one or more of the following compounds having the following structural formulas:

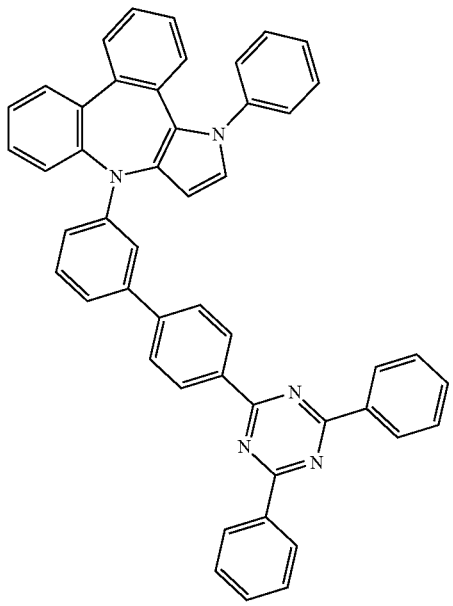

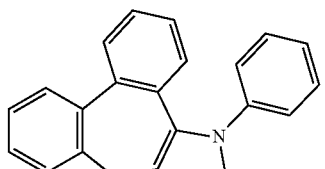

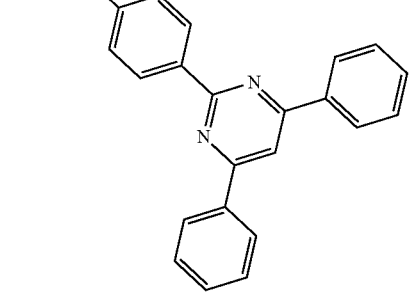

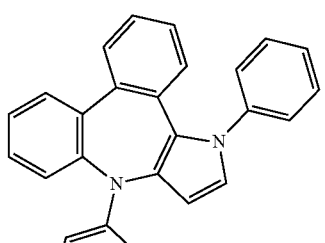

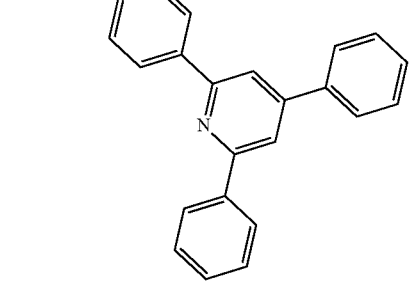

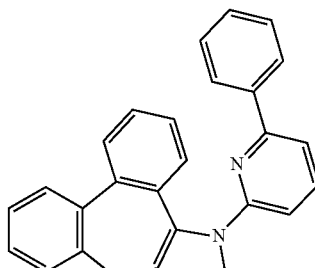

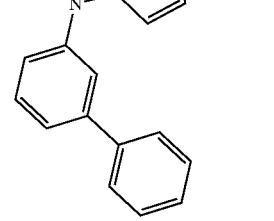

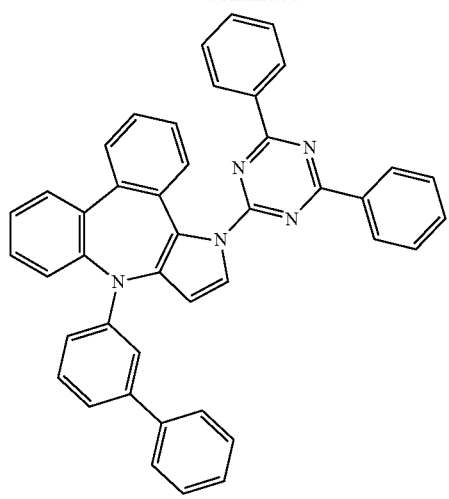
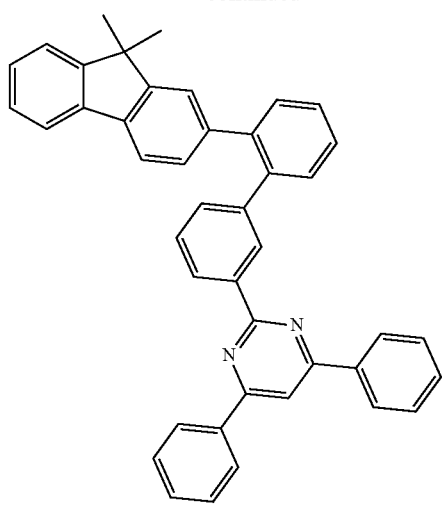
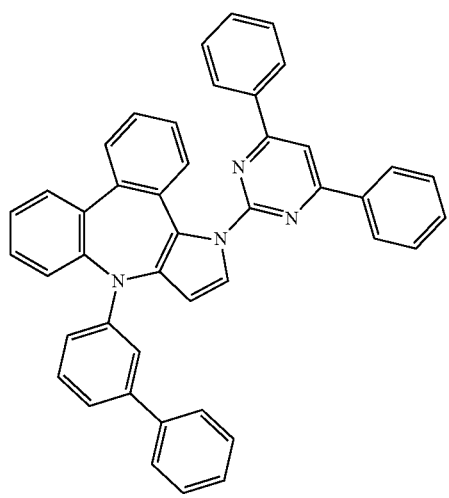
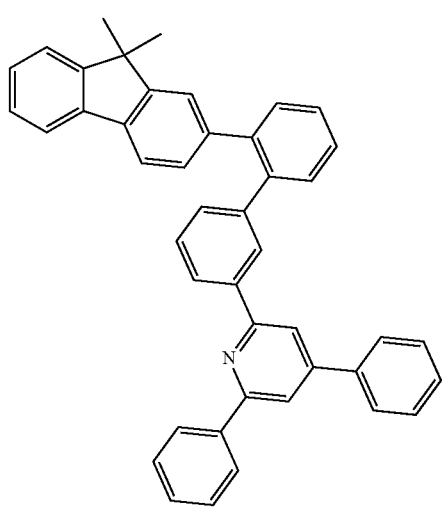
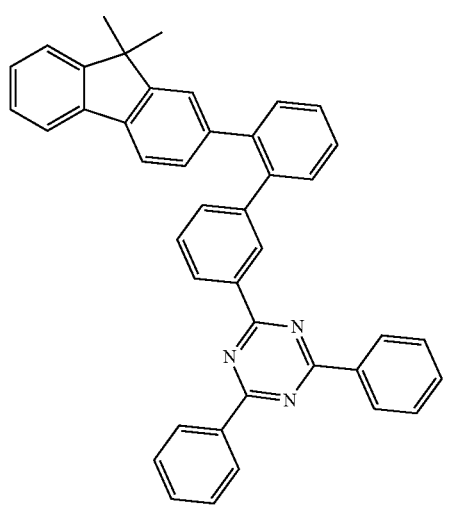
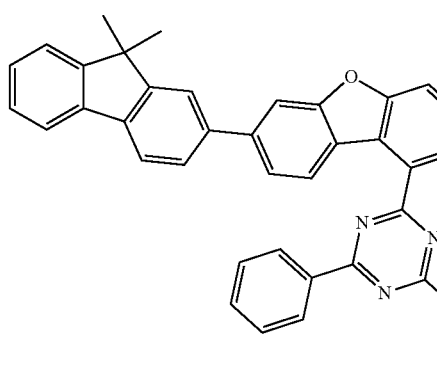

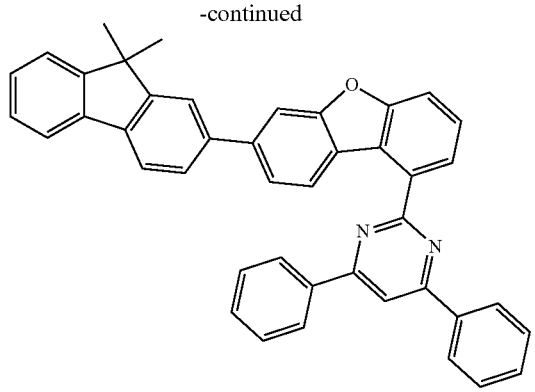

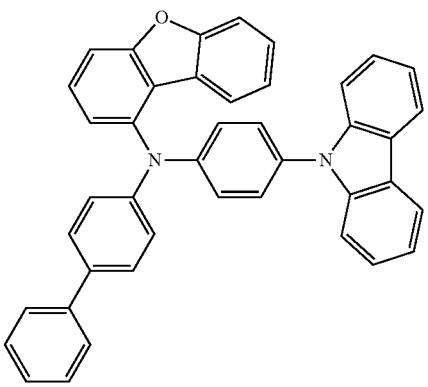

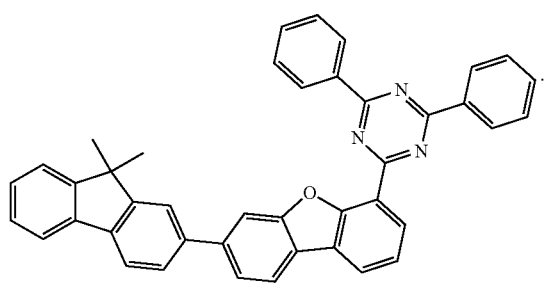

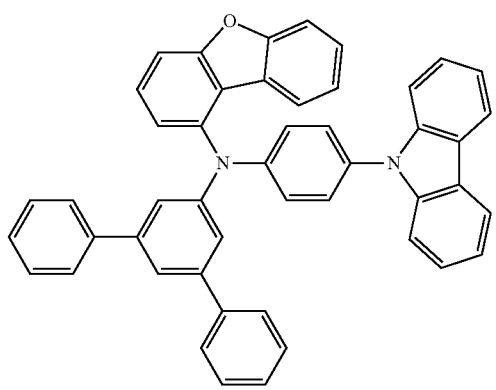

13. The organic light emitting device of claim 5, wherein a material of the electron block layer comprises one of the compounds having the following structural formulas:

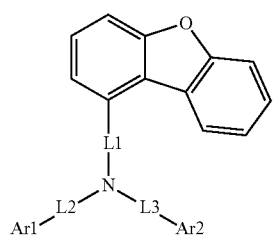

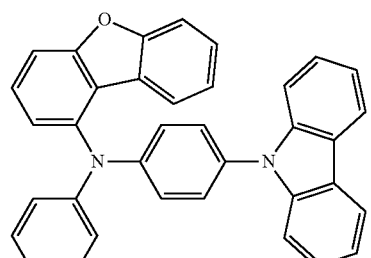

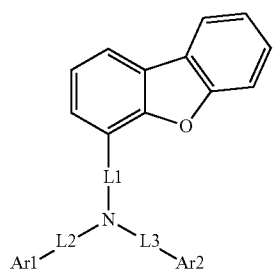

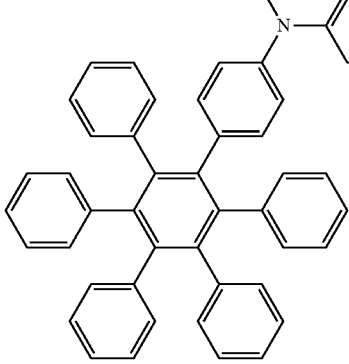

where L1-L3 are C6-C15 aryl; $Ar_1$, $Ar_2$ are C6-C40 aryl, arylamino, or fluorenyl, $Ar_1$ and $Ar_2$ are different groups.

14. The organic light emitting device of claim 13, wherein a material of the electron block layer comprises one or more compounds having the following structural formulas.

73
-continued
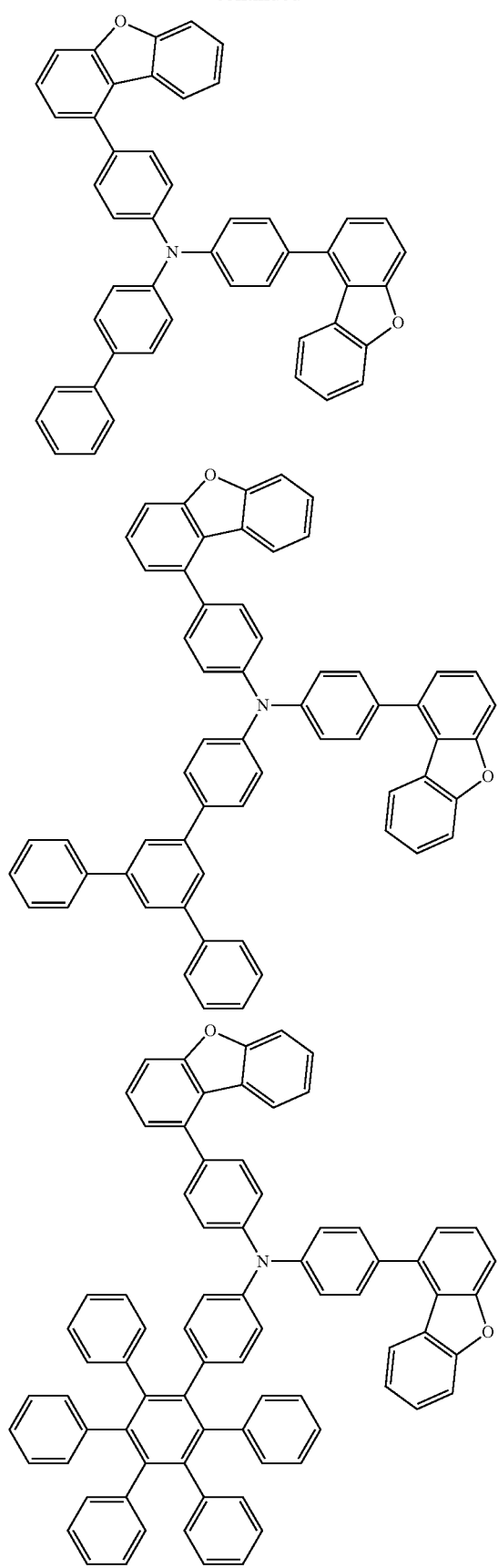
74
-continued
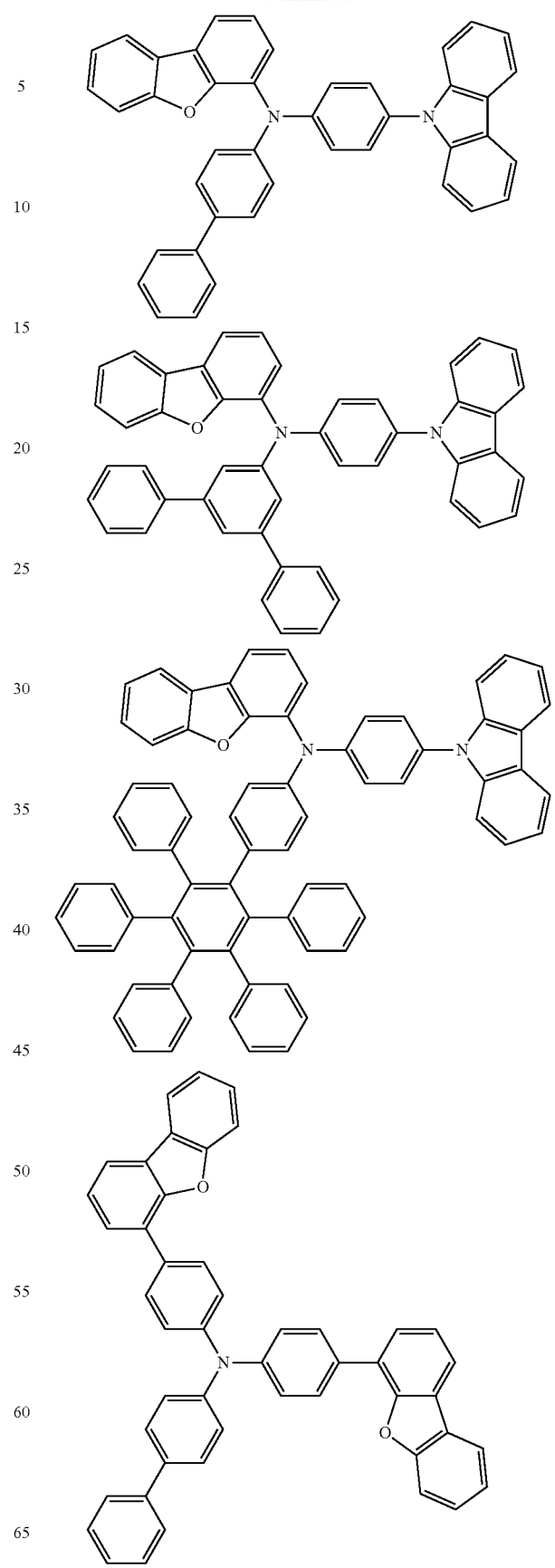

-continued

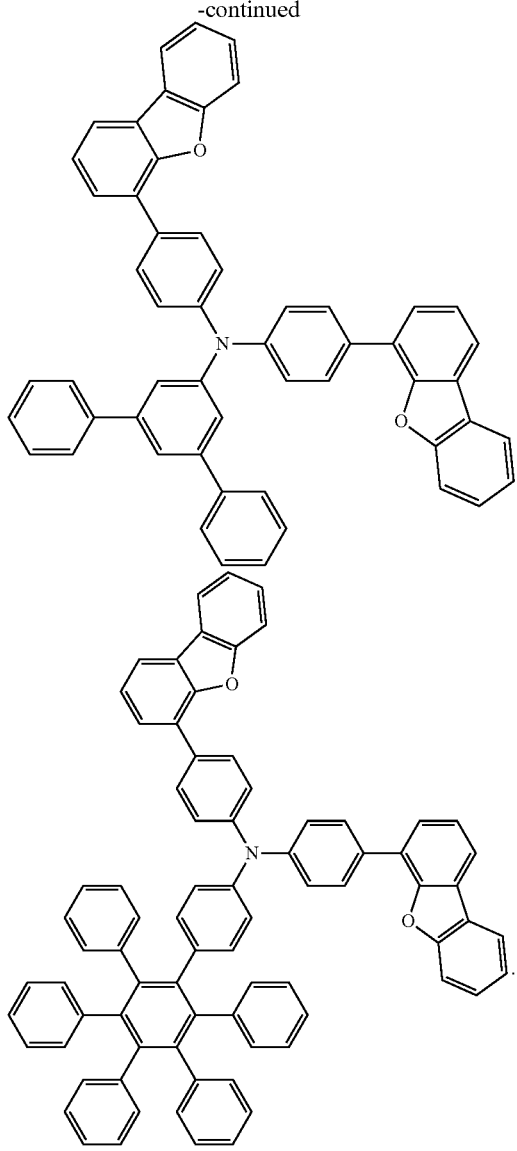

15. The organic light emitting device of claim 13, wherein one of $Ar_1$ and $Ar_2$ is a substituent represented by the following structural formula:

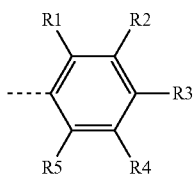

where R1-R5 are hydrogen, deuterium, alkyl, cycloalkyl, or C6-C36 aryl;

or one of $Ar_1$ and $Ar_2$ is a substituent represented by the following structural formulas:

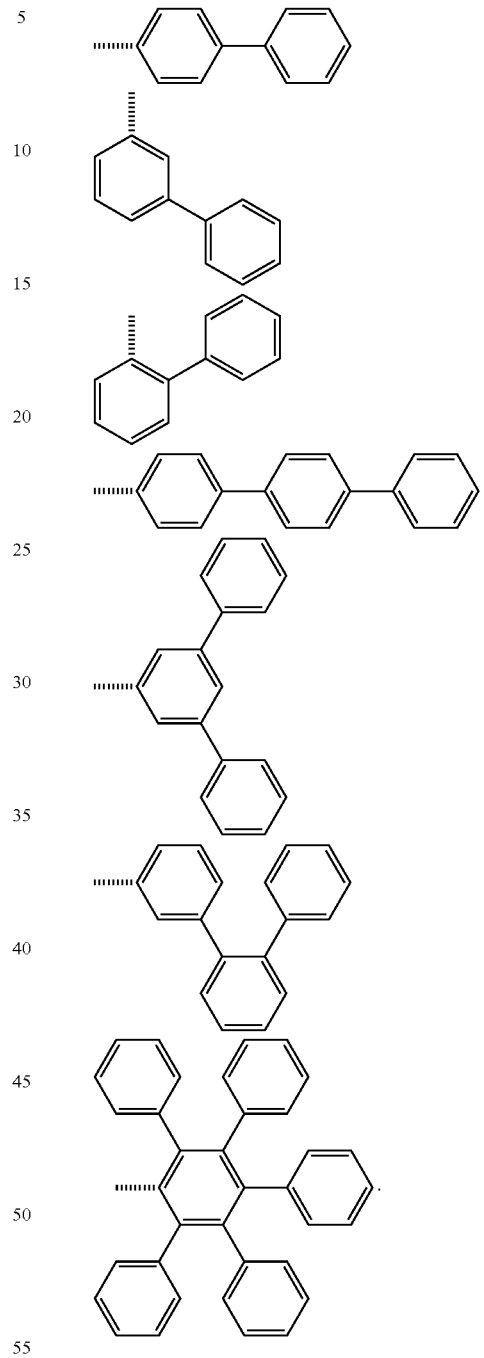

16. A display apparatus comprising the organic light emitting device of claim 1.

* * * * *

UNITED STATES PATENT AND TRADEMARK OFFICE
CERTIFICATE OF CORRECTION

PATENT NO. : 12,178,063 B2
APPLICATION NO. : 17/429359
DATED : December 24, 2024
INVENTOR(S) : Lixia Qiu, Lei Chen and Yang Liu It is certified that error appears in the above-identified patent and that said Letters Patent is hereby corrected as shown below:

On the Title Page

Foreign Application Priority Data should be added:
Oct. 23, 2020 (CN) .............. PCT/CN2020/123375

Signed and Sealed this
Twenty-eighth Day of January, 2025

Coke Morgan Stewart
*Acting Director of the United States Patent and Trademark Office*